United States Patent [19]

Cartwright et al.

[11] Patent Number: 4,778,914

[45] Date of Patent: Oct. 18, 1988

[54] CHEMICAL INTERMEDIATES

[75] Inventors: David Cartwright, Reading; David J. Collins, Crowthorne, both of England

[73] Assignee: Imperial Chemical Industries PLC, London, England

[21] Appl. No.: 831,061

[22] Filed: Feb. 19, 1986

Related U.S. Application Data

[63] Continuation of Ser. No. 503,544, Jun. 13, 1983, abandoned, which is a continuation-in-part of Ser. No. 224,823, Jan. 13, 1981, Pat. No. 4,388,472, which is a continuation-in-part of Ser. No. 168,783, Jul. 14, 1980, abandoned.

[30] Foreign Application Priority Data

Jul. 18, 1979 [GB] United Kingdom ............... 7925035
Jul. 1, 1980 [GB] United Kingdom ............... 8021545
Apr. 7, 1983 [GB] United Kingdom ............... 8309397

[51] Int. Cl.$^4$ ............................................. C07C 69/76
[52] U.S. Cl. .................................... 560/21; 544/54; 544/58.2; 544/158; 544/176; 548/255; 548/263; 548/337; 548/375; 548/538; 546/245; 558/257; 560/65; 564/166; 564/255
[58] Field of Search ............. 560/21, 65; 544/54, 544/58.2, 158, 176; 548/255, 263, 337, 375, 538; 546/245; 558/257; 564/166, 255

[56] References Cited

U.S. PATENT DOCUMENTS

| | | | |
|---|---|---|---|
| 3,784,635 | 1/1974 | Theissen | 560/21 |
| 4,063,929 | 12/1977 | Bayer | 560/21 |
| 4,093,446 | 6/1978 | Bayer et al. | 71/109 |

FOREIGN PATENT DOCUMENTS

| | | | |
|---|---|---|---|
| 2304006 | 8/1973 | Fed. Rep. of Germany | 560/21 |
| 50-71826 | 6/1975 | Japan | 560/21 |

Primary Examiner—Paul J. Killos
Attorney, Agent, or Firm—Cushman, Darby & Cushman

[57] ABSTRACT

Herbicidal mixtures comprising (1) a diphenyl ether of the formula:

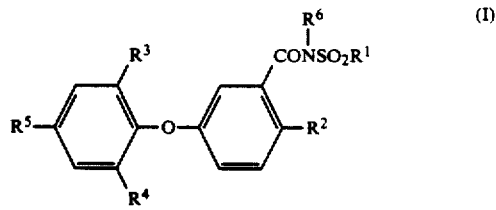

or a salt thereof, wherein $R^1$ is, for example, alkyl; $R^2$ is hydrogen, halogen or nitro; $R^3$ is hydrogen, halogen, alkyl, trifluoromethyl or cyano; $R^4$ is hydrogen, halogen or trifluoromethyl; $R^5$ is hydrogen, halogen or trifluoromethyl and $R^6$ is hydrogen or alkyl of 1 to 6 carbons and (2) another herbicide not of formula (I). Intermediates for preparing the formula (I) compounds and processes for using these compounds are also disclosed.

4 Claims, No Drawings

CHEMICAL INTERMEDIATES

This is a continuation of application Ser. No. 503,544, filed June 13, 1983, abandoned, which is itself a continuation-in-part of Ser. No. 224,823, filed Jan. 13, 1981, now U.S. Pat. No. 4,388,472, which is a continuation-in-part of Ser. No. 168,783, filed July 14, 1980, abandoned.

This invention relates to herbicidal mixtures, to herbicidal compositions and processes utilising them, and to chemical intermediates useful for preparing active ingredients of the compositions.

One component of the mixtures of the invention comprises a compound of the formula (I) below. Compounds of this formula have been described and claimed in our European patent application having publication No. 0003416.

According to the present invention there are provided herbicidal mixtures comprising (1) at least one diphenyl ether compound of the formula (I):

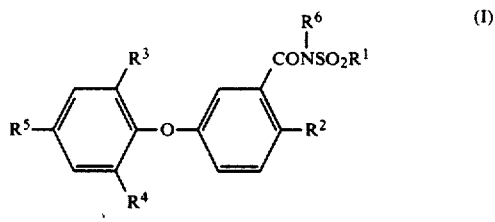

or a salt thereof, wherein $R^1$ is an alkyl group optionally substituted by one or more fluorine atoms or by an optionally substituted phenyl group; $R^2$ is a hydrogen atom, a fluorine, chlorine, bromine or iodine atom, or a nitro group; $R^3$ is a hydrogen atom, a fluorine, chlorine, bromine, or iodine atom, an alkyl group, a trifluoromethyl group, or a cyano group; $R^4$ is a hydrogen atom, a fluorine, chlorine, bromine, or iodine atom, or a trifluoromethyl group; $R^5$ is a fluorine, chlorine, bromine, or iodine atom or a trifluoromethyl group; and $R^6$ is a hydrogen atom or an alkyl group of 1 to 4 carbon atoms and (2) another herbicide not of the formula (I).

When either of the groups $R^1$ and $R^3$ is an alkyl group, it may be an alkyl group of, for example, 1 to 12 or more carbon atoms. Within this range, $R^1$ and $R^3$ may be, for example, an alkyl group of one to six carbon atoms, for example a methyl, ethyl, propyl, isopropyl, butyl, isobutyl, sec-butyl or t-butyl group.

When $R^1$ is an alkyl group substituted by phenyl it may be, for example, a benzyl group in which the phenyl radical may optionally be substituted, for example by one or more halogen atoms. When $R^1$ is a fluorine-substituted alkyl group, it may be for example an alkyl group of 1 to 6 carbon atoms substituted by one or more fluorine atoms; for example it may be a monofluoro-, difluoro-, or trifluoromethyl group.

Compounds of formula (I) include, for example, those in which $R^1$ is a methyl or ethyl group, $R^2$ is a nitro group, $R^3$ is a chlorine atom, $R^4$ is a hdyrogen atom, $R^5$ is a chlorine atom or a trifluoromethyl group, and $R^6$ is a hydrogen atom.

A further group of compounds of formula (I) are those in which $R^1$ is a methyl group; $R^2$ is a chlorine or bromine atom; $R^3$ is a chlorine atom; $R^4$ is a hydrogen atom; $R^5$ is a chlorine atom or a trifluoromethyl group; $R^6$ is a hydrogen atom.

Particular examples of compounds according to formula I are listed in Table I below:

TABLE 1

| COMPOUND NO | $R^1$ | $R^2$ | $R^3$ | $R^4$ | $R^5$ | $R^6$ | MELTING POINT °C. |
|---|---|---|---|---|---|---|---|
| 1 | CH$_3$ | NO$_2$ | Cl | H | CF$_3$ | H | 201 |
| 2 | C$_2$H$_5$ | NO$_2$ | Cl | H | CF$_3$ | H | 161.5 |
| 3 | C$_3$H$_7$ | NO$_2$ | Cl | H | CF$_3$ | H | 179 |
| 4 | C$_4$H$_9$ | NO$_2$ | Cl | H | CF$_3$ | H | 183 |
| 5 | C$_6$H$_{13}$ | NO$_2$ | Cl | H | CF$_3$ | H | 171 |
| 6 | CH$_3$ | NO$_2$ | Cl | H | CF$_3$ | CH$_3$ | 117 |
| 7 | CH$_3$ | Cl | Cl | H | CF$_3$ | H | 185.5 |
| 8 | CH$_3$ | Cl | Cl | H | CF$_3$ | CH$_3$ | 116 |
| 9 | CH$_3$ | Br | Cl | H | CF$_3$ | H | 164 |
| 10 | CH$_3$ | Br | Cl | H | CF$_3$ | CH$_3$ | 108 |
| 11 | CH$_3$ | H | Cl | H | CF$_3$ | H | 168 |
| 12 | C$_4$H$_9$ | H | Cl | H | CF$_3$ | H | 102 |
| 13 | CH$_2$C$_6$H$_5$ | H | Cl | H | CF$_3$ | H | 186.5 |
| 14 | CH$_3$ | H | H | H | CF$_3$ | H | 124.5-126 |
| 15 | CH$_3$ | H | CN | H | CF$_3$ | H | 198-199 |
| 16 | CH$_3$ | NO$_2$ | CN | H | CF$_3$ | H | 171-172 |
| 17 | CH$_3$ | NO$_2$ | Cl | H | Cl | H | 182-183 |
| 18 | C$_4$H$_9$ | NO$_2$ | Cl | H | Cl | H | 198-200 |
| 19 | CH$_3$ | H | Cl | H | Cl | H | 184-187 |
| 20 | CH$_3$ | Br | Cl | H | Cl | H | 146-147 |
| 21 | CH$_3$ | NO$_2$ | Cl | Cl | Cl | H | 227.5-228 |
| 22 | CH$_3$ | NO$_2$ | Br | Br | Br | H | 237-239 |
| 23 | CH$_3$ | NO$_2$ | CH$_3$ | H | Cl | H | 177.5-178.5 |
| 24 | isoC$_3$H$_7$ | NO$_2$ | Cl | H | CF$_3$ | H | 146 |
| 25 | CH$_3$ | H | CF$_3$ | H | Cl | H | 129-130 |
| 26 | CF$_3$ | NO$_2$ | Cl | H | CF$_3$ | H | 100 |
| 27 | C$_3$H$_7$ | Cl | Cl | H | CF$_3$ | H | 146 |
| 28 | C$_4$H$_9$ | Cl | Cl | H | CF$_3$ | H | 149.5 |
| 29 | CH$_3$ | NO$_2$ | F | Cl | Cl | H | 148-150 |
| 30 | CH$_3$ | I | Cl | H | CF$_3$ | H | 165-166 |
| 31 | CH$_3$ | NO$_2$ | Cl | CH$_3$ | Cl | H | 203-204 |
| 32 | CH$_3$ | NO$_2$ | Cl | H | F | H | 162-163 |
| 33 | CH$_3$ | F | Cl | H | CF$_3$ | H | 157-158 |
| 34 | CH$_3$ | NO$_2$ | Br | F | Br | H | 167-169.5 |
| 35 | CH$_3$ | H | Cl | H | Br | H | 184-185.5 |
| 36 | CH$_3$ | NO$_2$ | Br | H | CF$_3$ | H | 163-167 |
| 37 | CH$_3$ | NO$_2$ | H | H | CF$_3$ | H | 165-168 |
| 38 | CH$_3$ | NO$_2$ | F | H | CF$_3$ | H | 194-195 |

TABLE 1-continued

| COMPOUND NO | $R^1$ | $R^2$ | $R^3$ | $R^4$ | $R^5$ | $R^6$ | MELTING POINT °C. |
|---|---|---|---|---|---|---|---|
| 39 | $CH_3$ | $NO_2$ | $CF_3$ | H | $CF_3$ | H | 170–171 |
| 40 | $CH_3$ | $NO_2$ | Cl | Cl | Br | H | 196–199 |
| 41 | $CH_3$ | $NO_2$ | $CF_3$ | H | Cl | H | 155 |
| 42 | $CH_3$ | $NO_2$ | Cl | Cl | $CF_3$ | H | 242–243 |
| 43 | $CH_3$ | $NO_2$ | I | H | $CF_3$ | H | 211 |
| 44 | $CH_3$ | $NO_2$ | Cl | F | $CF_3$ | H | 171–172 |
| 45 | $CH_3$ | $NO_2$ | Cl | Br | $CF_3$ | H | 244–245 |
| 46 | $CH_3$ | $NO_2$ | Br | Br | $CF_3$ | H | 244–245 |
| 47 | $CH_3$ | H | $CF_3$ | H | $CF_3$ | H | 120 |
| 48 | $CH_3$ | $NO_2$ | F | F | $CF_3$ | H | 204–205 |
| 49 | $CH_3$ | $NO_2$ | $CH_3$ | H | $CF_3$ | H | 232–233 |
| 50 | $nC_4H_9$ | $NO_2$ | F | H | $CF_3$ | H | 165–166 |
| 51 | $CH_3$ | $NO_2$ | Br | Br | Cl | H | 221–223 |
| 52 | $CH_3$ | $NO_2$ | Cl | CN | $CF_3$ | H | 204–205 |
| 53 | $CH_3$ | $NO_2$ | Br | H | Br | H | 148–150 |
| 54 | $CH_3$ | Cl | F | Cl | $CF_3$ | H | 172–173 |
| 55 | $nC_4H_9$ | Cl | F | Cl | $CF_3$ | H | 139 |
| 56 | $CH_3$ | Cl | Cl | Cl | $CF_3$ | H | 195–196 |
| 57 | $nC_4H_9$ | Cl | Cl | Cl | $CF_3$ | H | 177 |
| 58 | $C_2H_5$ | $NO_2$ | F | Cl | $CF_3$ | H | 160–161 |
| 59 | $nC_3H_7$ | $NO_2$ | F | Cl | $CF_3$ | H | 153–154 |
| 60 | $nC_4H_9$ | $NO_2$ | F | Cl | $CF_3$ | H | 186–187 |
| 61 | $CH_3$ | H | F | Cl | $CF_3$ | H | 153–154 |
| 62 | $CH_3$ | H | F | F | $CF_3$ | H | 152–153 |
| 63 | $nC_3H_7$ | $NO_2$ | F | F | $CF_3$ | H | 148–149 |
| 64 | $CH_2CH_2C_6H_5$ | $NO_2$ | Cl | H | $CF_3$ | H | 166–168 |
| 65 | $CH_2CF_3$ | $NO_2$ | Cl | H | $CF_3$ | H | 127–130 |

Further examples of compounds falling within the scope of formula (I) include the following compound: 5-(4-bromo-2-chlorophenoxy)-2-nitro-N-methanesulphonylbenzamide Compounds of formula (I) wherein the group $R^6$ is a hydrogen atom are acids and form salts with bases. Both the acid and the salt forms of the compounds may be used as herbicides. Examples of salts include metal salts and salts formed from ammonium and substituted ammonium cations. Among the metal salts are those in which the metal cation is an alkali metal cation, for example sodium, potassium, or lithium, or an alkaline earth metal cation, for example calcium or magnesium. The substituted ammonium cations include mono-, di-, tri- and tetra-substituted ammonium cations in which the substituents may be for example an alkyl or alkenyl radical of 1 to 20 carbon atoms optionally containing one or more hydroxy, alkoxy or phenyl substituents. Particular examples of substituted ammonium cations include isopropylammonium, triethanolammonium, benzyltrimethylammonium, morpholinium, piperidinium, trimethylammonium, triethylammonium, methoxyethylammonium, dodecylammonium and octadecylammonium, and the ammonium salts derived from the commercially available mixtures of amines sold under the Trade Names Armeen 12D, Armeen 16D, Armeen 18D, Armeen C, Armeen S, Armeen T and Armeen O.

The compounds of formula (I) may be prepared by methods known in themselves. Thus, compounds wherein $R^6$ is hydrogen may be prepared by the method outlined in Scheme A.

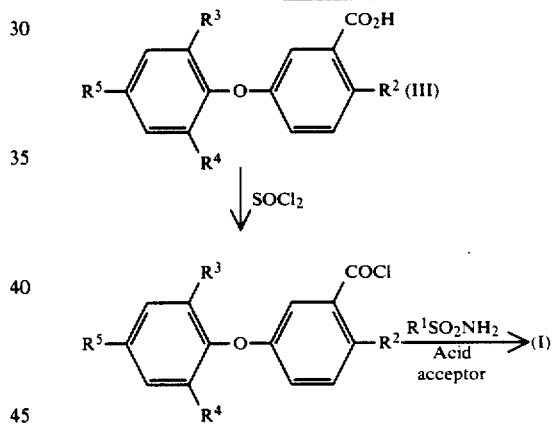

Scheme A

In Scheme A, an appropriately substituted carboxylic acid (III) is converted into the corresponding acid chloride (IV) by treatment with at least one molar proportion of thionyl chloride or another chlorinating agent, for example phosphorus oxychloride or phosphorous pentachloride, according to conventional procedures. The acid chloride (IV) so obtained is then treated with an alkane sulphonamide of formula $R^1SO_2NH_2$ in the presence of an acid acceptor to obtain the compounds of the formula (I). The sulphonamides $R^1SO_2NH_2$ are known or may be prepared by conventional methods.

The acid acceptor may be a tertiary amine, for example dimethylaniline or pyridine. The acid acceptor may also be an alkali metal carbonate, for example anhydrous sodium or potassium carbonate. Alkali metal fluorides may also be used, for example potassium fluoride or caesium fluoride. The reaction is preferably carried out in a solvent. Where pyridine is the acid acceptor, the solvent may conveniently comprise an excess of pyridine Other solvents include ketones, for example acetone, methyl ethyl ketone, and methyl isobutyl ketone, and esters, for example butyl acetate.

The reaction may be carried out in the temperature range from ambient temperatures to elevated temperatures, for example from 25° C. up to 150° C. The products (I) may be isolated by conventional methods.

The carboxylic acids (III) required for Scheme A are in a number of cases known; compounds not already described in the literature may, however, be prepared by methods analogous to those for the known compounds.

Compounds wherein the group $R^5$ is chlorine or a trifluoromethyl group, $R^3$ is hydrogen, halogen, or cyano, and $R^4$ is hydrogen, halogen or trifluoromethyl, may be prepared by reacting at an elevated temperature a trifluoromethyl benzene substituted in the 4-position with a chlorine or fluorine atom, (a) with meta-hydroxy benzoic acid in the presence of an alkaline agent, for example sodium or potassium carbonate or (b) with the di-sodium or di-potassium salt of meta-hydroxy benzoic acid. When this approach is used, the $R^2$ substituent required in the end-product (in the cases where $R^2$ is not hydrogen) may conveniently be introduced by halogenation or nitration of the diphenyl ether so obtained as illustrated in Examples 5 and 7. The reaction of the meta-hydroxy benzoic acid and the 4-chloro or fluoro-substituted trifluoromethyl benzene is generally carried out at a temperature of from about 50° C. to 180° C. in a polar aprotic organic solvent, for example dimethyl sulphoxide, dimethyl formamide, sulpholane, N-methyl-2-pyrrolidone, hexamethylphosphoric triamide, and similar solvents. Other solvents may also be used for example methyl ethyl ketone. The nitration of the diphenyl ether so obtained may be carried out in a conventional way, for example by using a nitrating agent such as nitric acid/sulphuric acid, or potassium nitrate/-sulphuric acid, optionally with a solvent such as ethylene dichloride, methylene dichloride, chloroform or perchloroethylene.

In a second approach for preparing the carboxylic acids (III), an ester, for example the methyl ester, of 5-halo-2-nitrobenzoic acid is reacted with a phenol of formula:

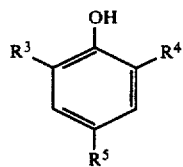

in the presence of a base such as sodium or potassium hydroxide or carbonate, or the like. The reaction is preferably carried out at a temperature of 50° C. to 180° C. in a dipolar aprotic solvent selected from those mentioned above or in a ketone (e.g. methyl ethyl ketone) or other convenient solvent which is inert to the reactants. This approach provides compounds of formula (III) in which the carboxy group is esterified. The ester group may be hydrolysed by standard procedures for example by treatment with acid or alkali to give compounds of formula (III) as illustrated in Example 8. This approach necesarily provides compounds (III) in which $R^2$ is a nitro group. If desired, the nitro group may be reduced by standard procedures to an amino group, diazotised, and converted into a bromine or chlorine substituent, as described in Example 10 thus providing compounds (III) in which $R^2$ is bromine or chlorine.

Similarly, the 2-iodo compound 30 was prepared by reducing the corresponding 2-nitro compound (i.e. compound no 1 of Table I) to the 2-amino derivative with titanium trichloride. The 2-amino derivative was dissolved in dilute sodium hydroxide containing sodium nitrite and added to aqueous fluoroboric acid to give the corresponding diazonium salt. This was filtered off as its fluoborate salt. The fluoborate was dissolved in acetone and treated with sodium iodide in acetone to give the 2-iodo compound no. 30.

The 2-fluoro compound 33 was obtained by a similar procedure starting with ethyl 5-(2-chloro-4-trifluoromethylphenoxy)-2-nitrobenzoate. This was reduced to the corresponding 2-amino compound with titanium trichloride the 2-amino compound diazotised, and diazonium salt isolated as its fluoborate. The diazonium fluoborate was heated to give ethyl 5-(2-chloro-4-trifluoromethylphenoxy)-2-fluorobenzoate. This was hydrolysed to the corresponding benzoic acid with sodium hydroxide solution at room temperature, and the benzoic acid converted to its acid chloride and reacted with methanesulphonamide to give compound no. 33 in the usual way.

A third approach to preparing the carboxylic acids (III) is to react a substituted 4-chloro-nitrobenzene with meta-hydroxy benzoic acid in the presence of a base as described in the first approach above. Thus reaction of 3,4-dichloronitrobenzene with meta-hydroxy benzoic acid gives 3-(2-chloro-4-nitrophenoxy)benzoic acid. The nitro group in this compound can then be reduced to an amino group by a conventional procedure, diazotised, and converted to a bromine or chlorine atom, as illustrated in Example 9.

Another method of preparing the carboxylic acids (III) wherein one or both of the groups $R^3$ and $R^4$ are halogen atoms and $R^5$ is a $CF_3$ group comprises reacting a 2-amino-4-trifluoromethyl-6-(hydrogen or halogen) substituted phenol (XI) with a 5-fluoro or chloro-2-nitrobenzoic acid ester as shown below:

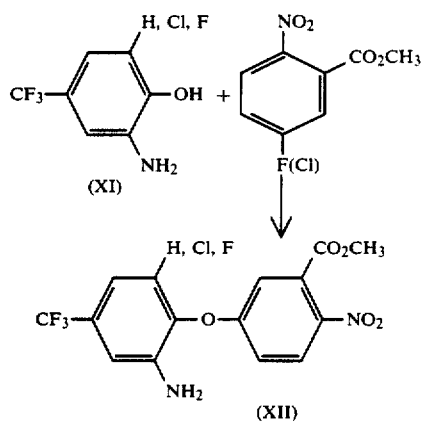

The reaction may be carried out using methyl ethyl ketone as a solvent and the anhydrous potassium carbonate as base. The reaction may be accelerated by heating. The amino group in the derivative (XII) may be diazotised and converted into a fluorine, chlorine, bromine or iodine substituent by conventional procedures. As illustrated in the last foregoing scheme, the final product of this process would be a methyl ester, for example the methyl 5(2-chloro-6-fluoro-4-trifluoromethylphenoxy)-2-nitrobenzoate described in Example 16 and methyl 5-(2,6-difluoro-4-trifluoromethylphenoxy)-2-nitrobenzoate described in Example 17. However, by using an ester of 5-fluoro-2-nitro benzoic acid or 5 -chloro-2-nitrobenzoic acid other than the methyl ester in the last foregoing scheme, different esters of the carboxylic acids (III, $R=NO_2$) may be obtained, for example the ethyl, propyl, butyl, pentyl, or hexyl esters. Whichever ester is chosen, it may be hydrolysed to the corresponding carboxylic acid (III, $R=NO_2$) by known procedures for example by heating with a mixture of aqueous hydrobromic acid and acetic acid. Mild alkaline hydrolysis, although less preferred, may also be employed, in which case the acids will be produced in the form of their salts (e.g. the sodium salt). The acids may be liberated from their salts by treatment with a mineral acid (e.g. hydrochloric or sulphuric acid). The carboxylic acids (III, $R=NO_2$) obtained by these procedures may then be converted to N-alkanesulphonylamide derivatives as shown in Scheme A above. Both 5(2-chloro-6-fluoro-4-trifluoromethylphenoxy)-2-nitrobenzoic acid and 5(2,6-difluoro-4-trifluoromethyl-phenoxy)-2-nitrobenzoic acid and their salts and esters are new compounds, and form a further feature of the present invention, being useful as intermediates for the preparation of the active ingredients (I) used in the compositions of the invention. In particular, 5(2-chloro-6-fluoro-4-trifluoromethylphenoxy)benzoic acid and its esters are useful as intermediates for the preparation of compound no. 44 of Table I. The compounds 5(2-chloro-6-fluoro-4-trifluoromethylphenoxy)-2-nitrobenzoic acid and 5(2,6-difluoro-4-trifluoromethylphenoxy)-2-nitrobenzoic acid and their salts and esters are themselves useful as herbicides which may be employed for example for the control of weeds in various crops (e.g. soyabean) at rates of application appropriate to the particular crop and weeds but usually in the range from 0.25 to 4 pounds of the compound per acre.

The 2-amino-4-trifluoromethylphenols (XI) required for the reaction sequence just described may be prepared by conventional methods. Thus 2-amino-6-fluoro-4-trifluoromethylphenol may be prepared from 2-nitro-4-trifluoromethylchlorobenzene by reacting the latter with sodium methoxide to give 2-nitro-4-trifluoromethylanilsole, and reducing this compound to 2-amino-4-trifluoromethylanisole. The latter compound may be diazotised and converted to its fluorborate salt and heated to give 2-fluoro-4-trifluoromethylanisole. This may then be nitrated to form 2-fluoro-6-nitro-4-trifluoromethyl anisole, which is then reduced to give 2-amino-6-fluoro-4-trifluoromethylanisole. Finally the latter compound is heated with a dimethylating agent, for example an excess of pyridine hydrochloride to give 2-amino-6-fluoro-4-trifluoromethylphenol.

By way of a further example, 2-amino-6-chloro-4-trifluoromethylphenol may be prepared from 3-chloro-4-hydroxybenzotrifluoride by nitrating the latter compound to give 3-chloro-4-hydroxy-5-nitrobenzotrifluoride. Reduction of the latter compound (for example with sodium dithionite) gives the required 2-amino-6-chloro-4-trifluoromethylphenol.

Compounds of formula (I) wherein $R^6$ is an alkyl group may be prepared from the corresponding compound wherein the group $R^6$ is a hydrogen atom, by reaction with diazoalkane. Thus where $R^6$ is a methyl group, the corresponding compound wherein $R^6$ is hydrogen may be reacted with diazomethane and the corresponding compound wherein $R^6$ is methyl recovered. The procedures for carrying out such methylation reactions are well known to those skilled in the art.

The compounds of formula (I) are useful both as pre- and post-emergence herbicides. Pre-emergence herbicides are usually used to treat the soil in which a crop is to be planted, by application before or during seeding, or after seeding and before the crop emerges. Post-emergence herbicides are applied after the crop plants have emerged from the soil. Compounds of formula (I) may be used as selective herbicides in a variety of crops, including for example cotton, soyabean, peanuts, sugarbeet, peas, wheat, barley and rice. They may also be used as total herbicides. They may be applied by any of the conventional techniques for applying herbicides. When applied as pre-emergence herbicides they may for example be sprayed on the soil before or during seedling, or after seeding and before emergence of the crop. In some situations for example in pre-emergence application to soya bean crops it may be advantageous to incorporate the compound of the invention into the soil before planting the crop. This may be done by applying the compound to the surface of the soil and then discing or harrowing the soil to mix the compound with the soil. Alternatively use may be made of the applicators which have been developed for placing herbicides in a band beneath the surface of the soil.

The second herbicidal component of the mixtures according to the invention may be a selective herbicide capable of being used in admixture with a compound of formula (I) to control weeds in crops, for example crops of soyabean, cotton, and peas. Alternatively, the second herbicidal component may be a non-selective herbicide chosen to enhance the power of the component of formula (I) as a total herbicide.

Examples of herbicides for use in admixture with compounds of formula (I) include the following:

A. Benzo-2,1,3-triadiazin-4-one-2,2-diaoxides, e.g. those formula:

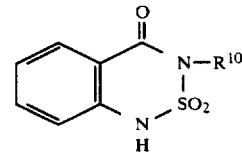

where $R^{10}$ is $C_{1-6}$ alkyl, in particular the compound in which $R^{10}$ is isopropyl, common name bentazon. Such mixtures are preferably applied post-emergence.

B. Aryloxyphenoxypropionic acids and their derivatives (salts, esters, amides and the like).

. Examples of such acids are:

2[3,5-dichloropyridyl-2-oxy]propionic acid
2[4(5-trifluoromethylpyridyl-2-oxy)phenoxy] acid
2[4(4-trifluoromethylphenoxy)phenoxy]propionic acid
2[4(2,4-dichlorophenoxy)phenoxy]propionic acid
2[4(6-chlorobenzoxazolyl-2-oxy)phenoxy]propionic acid
4-Methyl-4(4-trifluoromethylphenoxy)phenoxybut-2-enoic acid C. Dinitrophenols, for example those of formula:

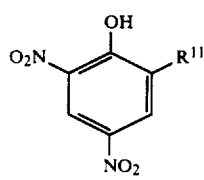

where $R^{11}$ is an alkyl group of 1 to 5 carbon atoms, and their derivatives, e.g. acetates; in particular such compounds wherein $R^{11}$ is methyl (common name DNOC), tert-butyl (common name dinoterb); or wherein $R^{11}$ is sec-butyl (common name dinoseb); and its ester dinoseb acetate. Mixtures with dinoseb may be used for example to control weeds in peanuts, and may be applied for example at the stage when the peanut plants are just breaking through the soil surface.

D. Dinitroaniline herbicides, for example those of formula:

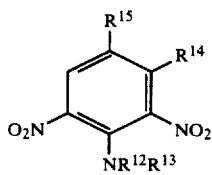

wherein $R^{12}$ is hydrogen or $C_{1-6}$ alkyl, cycloalkyl or alkenyl, optionally substituted with halogen. $R^{13}$ is $C_{1-6}$ alkyl; $R^{14}$ is hydrogen, methyl or amino; and $R^{15}$ is trifluoromethyl, $C_{1-6}$ alkyl, methyl sulphonyl or aminosulphonyl; in particular: N'N'-diethyl-2,6-dinitro-4-trifluoromethyl-m-phenyl-enediamine (common name dinitramine), 2,6-dinitro-NN-dipropyl-4-trifluoromethylaniline (common name trifluralin), 4-sulphonamido-2,6-dinitro-NN-dipropylaniline (common name oryzalin). Mixtures with these compounds may be applied pre-emergence or by incorporation into the soil before the crop is planted.

E. Phenylurea herbicides, e.g. of formula:

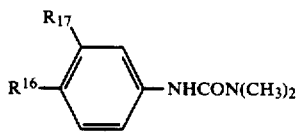

where $R^{16}$ and $R^{17}$ are independently hydrogen, chloro, $C_{1-4}$ alkyl or alkoxy, or trifluoromethyl; in particular the compound in which $R^{16}$ and $R^{17}$ are both chloro (common name diuron), the compound in which $R^{16}$ is hydrogen and $R^{17}$ is trifluoromethyl (common name fluometuron). These mixtures may be used for example in cotton crops.

F. 2-phenylpyridazin-3-ones, e.g. those of formula:

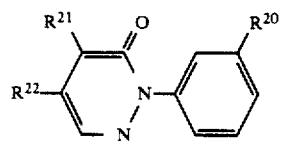

where $R^{20}$ is hydrogen or trifluoromethyl, $R^{21}$ is chloro, bromo or methoxy and $R^{22}$ is amino (optionally methyl substituted) or methoxy; particularly 5-amino-4-chloro-2-phenylpyridazine-3-one (common name pyrazon) and 4-chloro-5-(methylamino)-2-[3-trifluoromethylphenyl]-3(2H)-pyridazinone (common name norflurazon). The mixtures with norfluorazon may be used for example in cotton crops.

G. Triazine herbicides, for example of formula:

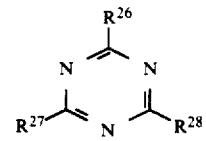

wherein $R^{26}$ is chloro, methoxy, methylthio or ethylthio; $R^{27}$ is $(C_{1-6})$ alkylamino, alkoxyalkylamino or dialkylamino; and $R^{28}$ is $(C_{1-6})$ alkylamino, alkoxyalkylamino, cyanoalkylamino, dialkylamino or azido; particularly:

2-chloro-4-ethylamino-6-isopropylamino-1,3,5-triazine (common name atrazine)

2-chloro-4,6-di(ethylamino)-1,3,5-triazine (common name simazine)

2-azido-4-isopropylamino-6-methylthio-1,3,5-triazine (common name aziprotryne)

2-chloro-4-(1-cyano-1-methylethylamino)-6-ethyl-amino-1,3,5-triazine (common name cyanazine).

Mixtures with cyanazine may be used, for example, in cotton.

H. 1-alkoxy-1-alkyl-3-phenylurea herbicides, e.g. of formula:

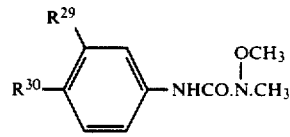

wherein $R^{29}$ is hydrogen or chloro and $R^{30}$ is chloro, bromo or ethoxy; in particular:

3-(3,4-dichlorophenyl)-1-methoxy-1-methylurea (common name linuron)

3-(4-chlorophenyl)-1-methoxy-1-methylurea (common name monolinuron)

3(4-bromo-4-chlorophenyl)-1-methoxy-1-methylurea (common name chlorobromuron)

I. Thiolcarbamate herbicides such as S-propyl dipropylthiocarbamate (common name vernolate). Such mixtures may be useful in weed control in peanuts.

J. 1,2,4-Triazine-5-one herbicides, e.g. of formula:

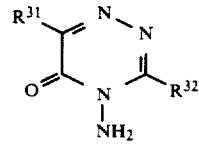

where $R^{31}$ is $C_{3-6}$ alkyl or cycloalkyl, or phenyl; and $R^{32}$ is methyl or methylthio; in particular:

4-amino-4,5-dihydro-3-methyl-6-phenyl-1,2,4-triazine-5-one (common name metamitron)

4-amino-6-tert-butyl-4,5-dihydro-3-methylthio-1,2,4-triazine-5-one (common name metribuzin).

Mixtures with metribuzin may be used as pre- or post-emergence herbicides in soya bean crops.

K. Benzoic acid herbicides, e.g. those of formula:

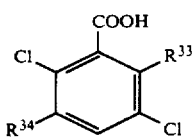

wherein $R^{33}$ is hydrogen, chloro or methoxy and $R^{34}$ is hydrogen or amino; especially 2,3,6-trichlorobenzoic acid (common name 2,3,6-TBA); 3,6-dichloro-2-methoxybenzoic acid (common name dicamba) and 3-amino-2,5-dichlorobenzoic acid (common name chloramben). Mixtures with chloramben may be used for example in soya bean crops.

L. Diphenylether herbicides, e.g. 4-nitrophenyl 2'-nitro-4-trifluoromethyl phenyl ether (common name fluorodifen); methyl-5-(2,4-dichlorophenoxy)-2-nitrobenzoate (common name bifenox); 2-nitro-5-(2-chloro-4-trifluoromethylphenoxy) benzoic acid as its sodium salt or methyl ester; and 2-chlorophenyl-3'-ethoxy-4'-nitro-4-trifluoromethyl phenyl ether.

M. Miscellaneous herbicides including N-chloroacetyl-N-methoxymethyl-2,6-diethylaniline (alachlor); N-chloroacetyl-N(3-methoxyprop-2-yl)-2,6-diethylaniline (metetilachlor); N,N-dimethyldiphenylacetamide (common name diphenamid); N-1-naphthylphthalamic acid (common name naptalam) and 3-amino-1,2,4-triazole. Mixtures with naptalam may be useful in crops of soya and peanuts.

N. Bipyridylium herbicides, for example, salts of the 1,1'-dimethyl-4,4'-bipyridylium ion (common name paraquat) and salts of the 1,1'-ethylene-2,2'-bipyridylium ion (common name diquat). Mixtures with these herbicides may be useful in the direct drilling of soya bean crops. The expression "direct drilling" refers to the procedure in which a crop is sown into an area of land without prior cultivation; the vegetation remaining from a previous crop is killed by treatment with a herbicide which does not affect the crop being sown.

O. Phosphonomethylglycine herbicides, for example salts and esters of N-phosphonomethylglycine (common name glyphosate). Mixtures with these herbicides may be useful in the direct drilling of soya bean crops.

P. Other miscellaneous herbicides include 1-acetamido-3-N-trifluoromethanesulphonamido-4,6-dimethylbenzene (trade name "Embark"); 4-benzenesulphonyl-2-methyl-N-methanesulphonylaniline (common name perfluidone); 3-phenyl-5-(3-trifluoromethylphenyl)-N-methyl-4-pyridone (common name fluridone) and the compound having the common name alloxydim-sodium, of which the chemical structure is shown below:

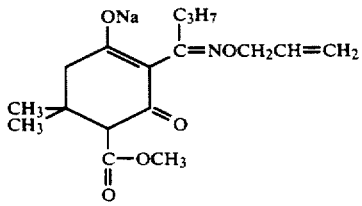

Mixtures containing perfluidone or fluridone may be useful for selective weed control in cotton. Another herbicide which may be mixed with compounds of formula (I) to provide mixtures for selective weed control in, for example, soya bean, is the compound 2-(1-ethoxyimino)butyl-5-(2-(ethylthio)propyl)-3-hydroxy-2-cyclohexene-1-one, also referred to by its code number NP55. Other herbicidal cyclohexen-1-one derivatives of formula similar to the above may also me mixed with compounds of formula (I).

Mixtures according to the invention generally contain from 0.1 to 20 parts, conveniently from 0.5 to 2 parts, by weight of herbicide of formula I per part by weight of other herbicide, depending on the relative activity of the components. In a number of cases the optimum benefit from the use of the combined herbicides results when the proportion of the herbicide of formula (I) is relatively high with respect to the other herbicide (e.g. from 10 to 20 parts by weight of herbicide of formula (I) per part by weight of other herbicide). Likewise, the amount of the mixture to be applied will depend upon a number of factors, for example the particular plant species whose growth is to be inhibited, but in general an amount of from 0.1 to 5 kilograms per hectare is usually suitable. The skilled worker in the art will readily be able to determine suitable ratios and amounts for use by means of standardised routine tests, without unduel experimentation.

The compounds used in the invention are preferably applied in the form of a composition, in which the active ingredients are mixed with a carrier comprising a solid or liquid diluent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth. Solid compositions also include soluble powders and granules which may comprise a salt of a compound of the invention in admixture with a water-soluble carrier, or a mixture of a compound of the invention wherein $R^6$ is hydrogen with an alkali for example sodium or potassium carbonate; wheñ mixed with water the composition gives a solution of a salt of the compound of the invention.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropylnaphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol, and octylcresol. Other nonionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredients. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

According to a further feature of the present invention there are provided diphenyl ether compounds of the formula (XIII):

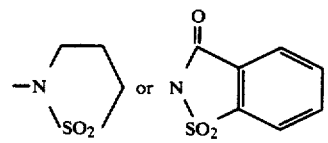

wherein X is a nitro group or a chlorine atom and R is:

(a) a group X'R³ wherein X' is oxygen or sulphur, and R³ is an aliphatic or alicyclic radical (eg. an aliphatic or alicyclic radical of 1 to 6 carbon atoms) bearing one or more of the following substituents: halogen; nitro; hydroxy; CF₃; alkoxy (eg. of 1 to 4 carbon atoms); alkylthio, alkylsulphinyl, or alkylsulphonyl each having for example from 1 to 4 carbon atoms; phenyl; heterocyclyl containing for example 5 or 6 ring atoms; a group —NR¹R² as defined below; cyano; carboxy or a salt thereof; alkoxycarbonyl (eg. having from 2 to 5 carbon atoms); a group —CONR¹R² wherein —NR¹R² is as defined below; formyl; alkanoyl having for example 2 to 5 carbon atoms; or a 1-pyrazolyl, 1-imidazolyl, 1-(1,2,4-triazolyl) or 2-(1,2,3-triazolyl) group optionally bearing one or more halogen, methyl, methoxy, or methylthio substituents.

(b) a group —NR¹R² wherein R¹ is hydrogen, an optionally substituted aliphatic or alicyclic radical (eg. an aliphatic radical of 1 to 6 carbon atoms or an alicyclic radical of 3 to 6 carbon atoms) or an optionally subtituted phenyl radical, and R² is defined as for R¹ but may additionally represent hydroxy; alkoxy of 1 to 4 carbon atoms; alkoxy of 1 to 4 carbon atoms substituted by phenyl or by carboxy or a salt, ester, or amide thereof; or alkoxy of 1 to 4 carbon atoms substituted by amino or mono- or di-dialkylamino wherein the alkyl groups have for example from 1 to 4 carbon atoms; or wherein the group —NR¹R² is constituted by an optionally methyl-substituted pyrrolidine, piperidine, or morpholine ring, or by a succinimido, or phthalimido radical or by a group of the formula:

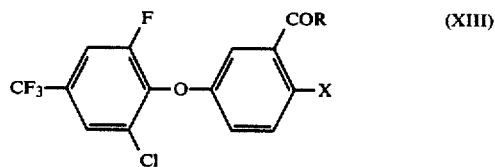

or (c) a phenoxy, phenylthio, 2-nitrophenoxy, or 2-sulpholanoxy group, or a group —ON=C(CH₃)₂.

The term halogen in the foregoing definition is intended to include fluorine, chlorine, bromine, and iodine. The term aliphatic is intended to include alkyl, alkenyl, and alkynyl radicals, whether straight chain or branched, and corresponding radicals with more than one double or triple bond. It is also intended to include radicals which comprise an alkyl, alkenyl, or alkynyl radical bearing an alicyclic radical as a substituent. The term alicyclic radical includes for example cycloalkyl radicals, for example cyclopropyl and cyclohexyl. When R¹ or R² is an aliphatic or alicyclic radical, possible substituents include, for example, halogen; hydroxy; alkoxy (eg. of 1 to 4 carbon atoms); cyano; phenyl; or heterocyclyl of 5 to 7 ring atoms. When R¹ or R² is a phenyl or heterocyclyl radical, examples of possible substituents include those recited above for the case when one of R¹ or R² is aliphatic or alicyclic, and further include alkyl (eg. of 1 to 4 carbon atoms), nitro, CF₃, and alkylthio, alkyl-sulphinyl, and alkylsulphonyl, each of 1 to 4 carbon atoms.

Where the foregoing definition includes reference to salts, esters, or amides of a carboxy group, the salts referred to are agriculturally acceptable salts, for example salts formed from alkali metal, alkaline earth metal, ammonium, or substituted ammonium cations; for example from sodium, potassium, lithium, calcium, or magnesium cations. Esters of the said carboxy groups include esters formed from aliphatic and alicyclic alcohols. Amides include those formed from ammonia or monoalkyl or dialkylamines wherein the alkyl groups each contain from 1 to 6 carbon atoms.

Particular examples of compounds falling within the scope of the invention are listed in Table 2 below:

TABLE 2

| Compound No. | X | R |
|---|---|---|
| 1 | NO₂ | —OCH₂CH₂Cl |
| 2 | Cl | —OCH₂CH₂Cl |
| 3 | NO₂ | —OCH₂CH₂NO₂ |
| 4 | Cl | —OCH₂CH₂NO₂ |
| 5 | NO₂ |  |
| 6 | Cl |  |
| 7 | NO₂ |  |
| 8 | Cl |  |
| 9 | NO₂ |  |
| 10 | Cl |  |
| 11 | NO₂ |  |
| 12 | Cl |  |
| 13 | NO₂ |  |
| 14 | Cl |  |
| 15 | NO₂ |  |
| 16 | Cl |  |

TABLE 2-continued

| Compound No. | X | R |
|---|---|---|
| 17 | NO₂ | —OCH₂-N(triazole) |
| 18 | Cl | —OCH₂-N(triazole) |
| 19 | NO₂ | —OCH₂-N-pyrazole-Cl |
| 20 | Cl | —OCH₂-N-pyrazole-Cl |
| 21 | NO₂ | —CH₂CH₂-N-pyrazole |
| 22 | Cl | —OCH₂CH₂-N-pyrazole |
| 23 | NO₂ | —OCH₂C(CH₃)₂-N-triazole |
| 24 | Cl | —OCH₂C(CH₃)₂-N-triazole |
| 25 | NO₂ | —OCH₂CO₂H |
| 26 | Cl | —OCH₂CO₂H |
| 27 | NO₂ | —OCH(CH₃)CO₂C₂H₅ |
| 28 | Cl | —OCH(CH₃)CO₂C₂H₅ |
| 29 | NO₂ | —OC₆H₅ |
| 30 | Cl | —OC₆H₅ |
| 31 | NO₂ | 2-NO₂.C₆H₄.O— |
| 32 | Cl | 2-NO₂.C₆H₄.O— |
| 33 | NO₂ | —O-tetrahydrothiophene-SO₂ |
| 34 | Cl | —O-tetrahydrothiophene-SO₂ |
| 35 | NO₂ | —NH₂ |
| 36 | Cl | —NH₂ |
| 37 | NO₂ | —ON═C(CH₃)₂ |
| 38 | Cl | —ON═C(CH₃)₂ |
| 39 | NO₂ | —NHCH₃ |
| 40 | Cl | —NHCH₃ |
| 41 | NO₂ | —N(CH₃)(OCH₃) |

TABLE 2-continued

| Compound No. | X | R |
|---|---|---|
| 42 | Cl | —N(CH₃)(OCH₃) |
| 43 | NO₂ | —NHOCH₂CO₂H |
| 44 | Cl | —NHOCH₂CO₂H |
| 45 | NO₂ | —NHOCH₂CO₂C₂H₅ |
| 46 | Cl | —NHOCH₂CO₂C₂H₅ |
| 47 | NO₂ | succinimido |
| 48 | Cl | succinimido |
| 49 | NO₂ | —N(CH₂CH₂CH₂)SO₂ (sulfolanyl) |
| 50 | Cl | —N(CH₂CH₂CH₂)SO₂ |
| 51 | NO₂ | saccharinyl |
| 52 | Cl | saccharinyl | where a compound falling within the scope of formula (I) above is capable of existing in optically isomeric forms, the invention includes the separate D and L forms of the compounds as well as mixtures of the D and L forms in all proportions. As normally prepared by chemical synthesis, such optically isomeric compounds will normally be obtained as mixtures of equal proportions of the D and L forms (ie. racemic mixtures).

The compounds of the invention may be prepared in various ways, for example by the process outlined in Scheme B below:

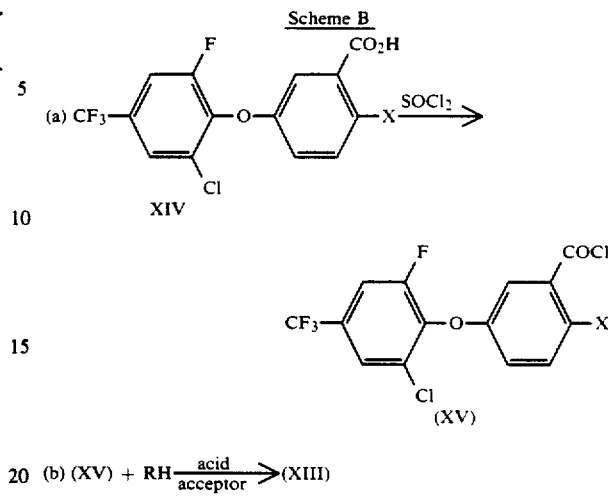

Scheme B (a) [XIV structure] $\xrightarrow{SOCl_2}$

[XV structure]

(b) (XV) + RH $\xrightarrow[\text{acceptor}]{\text{acid}}$ (XIII)

In Scheme B, the symbols R and X have the meanings previously assigned to them. The preparation of the carboxylic acids XIV required as starting materials is described herein. The other reactants RH are also in general known compounds or, where new in themselves, may be prepared by methods known for the preparation of the analogous known compounds. According to Scheme B, a carboxylic acid XIV is treated with thionyl chloride to convert it to the acid chloride (XV). Usually the reaction may be carried out by heating the carboxylic acid (XIV) under reflux with excess of thionyl chloride and removing the excess of thionyl chlorine under reduced pressure when reaction is complete. The acid is then reacted with the compound RH, preferably in a solvent or diluent inert towards the reactants, and preferably in the presence of an acid acceptor.

Depending upon the particular reactant RH chosen for use, the reaction mixture may be heated to accelerate the reaction, for example to a temperature in the range from 30°–130° C. or above. In some cases, it may be desirable to cool the reaction mixture at the start in order to moderate a vigorous exothermic reaction. The solvent or diluent may be for example a liquid hydrocarbon, for example diethyl ether or tetrahydrofuran; or a ketone, for example methyl ethyl ketone. Other solvents and diluents will be known to those skilled in the art; the choice of solvent or diluent is not critical. The acid acceptor is preferably present in at least an equimolar amount with respect to the reactants. Examples of acid acceptors include tertiary amines, for example pyridine, dimethylaniline, and triethylamine and inorganic bases, for example sodium or potassium carbonate. The product may be isolated from the reaction by conventional methods.

An alternative method of preparing the compounds of the invention is outlined in Scheme C below:

Scheme C (a) 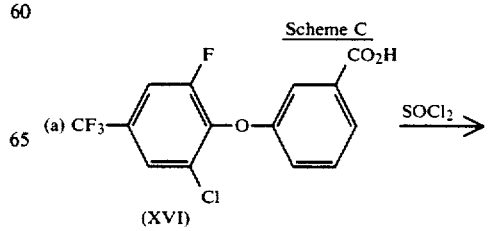 $\xrightarrow{SOCl_2}$ (XVI)

-continued
Scheme C

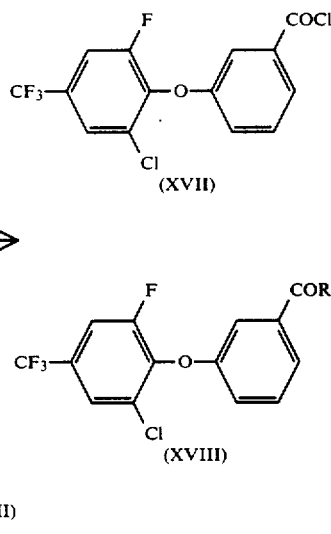

According to Scheme C, the carboxylic acid (XVI) is converted to the corresponding acid chloride (V) as described in Scheme B. The acid chloride is then reacted with the appropriate intermediate RH also as described in Scheme B. The product (XVIII) so obtained is then converted to the required compound (XIII) by nitration or chlorination. Thus, where X is to be a nitro group, the diphenyl ether (XVIII) is treated with a nitrating agent, for example a mixture of nitric and sulphuric acids, or potassium nitrate/sulphuric acid. Where X is to be chlorine, the diphenyl ether (XVIII) is treated with a chlorinating agent; for example, the diphenyl ether may be dissolved in a solvent (eg. glacial acetic acid) and treated with gaseous chlorine. In either case the required compound (XIII) is isolated from the reaction mixture by conventional methods.

The compounds of the invention are useful as herbicides. In yet another aspect, therefore, the invention provides a process of inhibiting the growth of unwanted plants, which comprises applying to the plants, or to the locus thereof, a phytotoxic amount of a compound of the formula (XIII) as hereinbefore defined. The amount of the compound to be applied in the process may vary, depending upon the particular compound chosen, and the identity of the plant species whose growth is to be inhibited, but in general amounts from 0.1 to 10 kilograms per hectare will be suitable; in many cases from 0.25 to 1.0 kilograms per hectare will be appropriate. The skilled worker in the herbicide art will readily be able to establish appropriate application rates by standard procedures without undue experimentation.

The compounds of the invention are effective in controlling a variety of unwanted plants. The compounds may be applied to the above-ground parts of unwanted plants (post-emergency application) or they may be applied to the soil to prevent the growth of plants from seeds present in the soil (pre-emergence application). The compounds may be used, for example, for selective weed control in crops of soya bean.

The compounds used in the process of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (I) as hereinbefore defined, in admixture with a solid or liquid diluent. Preferably the composition also comprises a surface-active agent. The compositions may take any of the forms described earlier in this specification in the case of mixtures containing a compound of the formula (I). Furthermore the compounds of formula XIII may be applied in admixture with any of the herbicides described in paragraphs A to P above.

The invention is illustrated by the following Examples, in which all parts are by weight and all temperatures in degrees Centigrade unless otherwise stated. Examples 1 to 21 are not examples of the invention but describe the preparation of compounds of formula (I).

EXAMPLE 1

This Example illustrates the preparation of compound no 1 of Table 1.

5(2-chloro-4-trifluoromethylphenoxy)-2-nitrobenzoic acid (1.58 g) was heated under reflux in an excess of thionyl chloride (20 ml) for 90 minutes. The excess of thionyl chloride was removed in a vacuum and the remaining oil taken up in dry pyridine (20 ml). Methanesulphonamide (0.45 g) was added and the mixture stirred at room temperature overnight. The pyridine was removed in a vacuum and the remaining oil mixed with 2-molar hydrochloric acid and extracted with ether (2×100 ml). The ether extracts were washed with water (100 ml), dried, and evaporated in a vacuum. The residual solid was recrystallised from isopropanol to give 5-(2-chloro-4-trifluoromethylphenoxy)-2-nitro-N-methanesulphonyl benzamide (Compound no 1) with a melting point of 201° C. In a similar way, but using the appropriate carboxy-substituted diphenyl ether and the appropriate sulphonamide in place of methanesulphonamide, the compounds listed in Table 1 were prepared, except for compounds 6, 8 and 10, whose preparation is described in Example 3.

EXAMPLE 2

This Example illustrates a method of preparing compound no 1 of Table 1 alternative to that described in Example 1.

3-(2-Chloro-4-trifluoromethylphenoxy)benzoic acid (20.5 g) was taken up in thionyl chloride (50 ml) and heated under reflux for 2 hours. The excess of thionyl chloride was removed under reduced pressure. The acid chloride which remained was stirred and cooled in ice and salt while dry, cooled pyridine (50 ml) was added. After 5 minutes, methanesulphonamide (6.4 g) was added. When it had dissolved, the ice and salt bath was removed and the mixture was left at room temperature overnight. The pyridine was then removed under reduced pressure. The residue was washed with water and dissolved in ethyl acetate. The solution was washed with 2-molar hydrochloric acid, then with water, dried, and evaporated. The residue (22 g) was recrystallised from a mixture of ethyl acetate and petroleum ether (b.p. 60°–80°) giving 3-(2-chloro-4-trifluoromethyl)-N-methanesulphonyl benzamide with a melting point of 173°–174°.

The benzamide derivative so prepared (1.6 g) was added to a mixture of concentrated sulphuric acid (6.4 ml) and dichloroethane (4 ml) which was stirred and kept at 0° C. in an ice and salt bath. After 5 minutes, potassium nitrate (0.51 g) was added in portions over a period of 15 minutes. The mixture was stirred for a further 45 minutes at 0° C. and then stored at −18° C. overnight. The mixture was poured into ice and water (60 ml) and then extracted with ethyl acetate. The ethyl acetate extract was washed with water, dried, and evaporated. The residue was crystallised twice from a mixture of ethyl acetate and petroleum ether (b.p. 60°-80°) and gave compound 1 (1.0 g) identified by its melting point and spectral properties with the compound made in Example 1.

EXAMPLE 3

This Example illustrates the preparation of compounds nos 6, 8 and 10 of Table 1. Compound no 1 (1.8 g) in diethyl ether (50 ml) containing a little methanol was cooled to 0° C. while a solution of diazomethane in ether was added until the yellow colour of the solution did not disappear after addition. The solution was left overnight at room temperature and a drop of glacial acetic acid was added to destroy excess of diazomethane. The solvent was removed and the remaining oil taken up in ethyl acetate and the solution washed with sodium bicarbonate solution and then with water, dried and evaporated to yield an oil. This was extracted with boiling petroleum (b.p. 60°-80° C.). The cooled extracts deposited an oil. This was dissolved in the minimum of diethyl ether and left to stand. The white solid which separated was collected and dried to give compound no 6 (0.5 g). Compounds 8 and 10 were prepared in a similar way, using diazomethane and compounds nos 7 and 9 respectively as starting materials.

EXAMPLE 4

This Example illustrates the preparation of 2-chloro-5(2-chloro-4-trifluoromethylphenoxy)benzoic acid.

A solution of 3(2-chloro-4-trifluoromethylphenoxy)benzoic acid (5 g) in glacial acetic acid (30 ml) was heated under reflux while chlorine was passed through the solution for 5 hours. The solution was left to stand for two days at room temperature and then poured into cold water (500 ml). An off-white gummy solid separated. This was extracted with ethyl acetate and the extract dried and evaporated. The brown oil remaining was dissolved in sodium bicarbonate solution and the solution extracted with ethyl acetate. The aqueous solution was acidified with hydrochloric acid. The solution was decanted from the precipitated gum, and the gum taken up in boiling hexane. The hexane solution was filtered and allowed to cool. The required 2-chloro-5(2-chloro-4-trifluoromethylphenoxy)benzoic acid was obtained (1.0 g) as crystals of melting point 103°-104°. This acid was used as starting material for compounds 7 and 8.

EXAMPLE 5

This Example illustrates the preparation of 2-bromo-5(2-chloro-4-trifluoromethylphenoxy)benzoic acid.

Methyl 3(2-chloro-4-trifluoromethylphenoxy)benzoate (10 g) was heated under reflux in glacial acetic acid (50 ml) while bromine (19.4 g) was added dropwise over a period of 1 hour. The mixture was heated under reflux for a further 4 hours, and further bromine (20 g) added. The mixture was heated for a further 8 hours under reflux. The acetic acid and excess of bromine were evaporated off and the residue taken up in water and brought to pH7 with sodium bicarbonate. The solution was extracted with ether and then acidified. The gummy white solid which separated was extracted with dichloromethane. The dichloromethane solution was dried and evaporated to give a white solid. This was identified as 2-bromo-5(2-chloro-4-trifluoromethylphenoxy)benzoic acid. This acid (8 g) was heated under reflux for 2½ hours in thionyl chloride (80 ml) and the excess of thionyl chloride then removed. The residue was treated at 10° C. with a solution of sodium (0.6 g) dissolved in methanol (40 ml) and then heated under reflux for 1 hour. The solvent was removed and the residue shaken with water and ether. Distillation of the ether solution gave the required methyl ester (5.2 g) with a boiling range of 152°-154°/0.1 Torr. Alkaline hydrolysis of this ester gave the carboxylic acid required as starting material for the preparation of compounds 9 and 10 of Table 1.

EXAMPLE 6

This Example illustrates the preparation of 3(4-trifluoromethylphenoxy)benzoic acid.

3-Hydroxybenzoic acid (6.9 g) was added in portions to potassium hydroxide (6.9 g) in solution in dry methanol (30 ml), with stirring. When addition was complete, the mixture was left for 15 minutes at room temperature and then the solvent removed under reduced pressure. The residue was dissolved in dimethylsulphoxide (30 ml) and anhydrous potassium carbonate (2.5 g) was added, followed by p-chlorobenzotrifluoride (9.03 g) in dimethyl sulphoxide (10 ml) dropwise, with stirring. The mixture was stirred and heated at 115° C. for 20 hours, then cooled and poured into water. The mixture was extracted twice with ethyl acetate and the aqueous solution then brought to pH2 with concentrated hydrochloric acid. The solid which separated was dried and washed with petroleum (b.p. 40°-60° C.) and recrystallised from a mixture of toluene and petroleum to give 6.6 g of the required 3-(4-trifluoromethylphenoxy)benzoic acid having a melting point of 140°-142° C., which was used as a starting material for compound no 14 of Table 1.

EXAMPLE 7

This Example illustrates the preparation of 5-(2-cyano-4-trifluoromethylphenoxy)benzoic acid, used as the starting material for compound no 15 of Table 1, and of 2-nitro-5-(2-cyano-4-trifluoromethylphenoxy)benzoic acid, useful as the starting material for compound 16.

(a) Preparation of 3-(2-cyano-4-trifluoromethylphenoxy)benzoic acid

3-Hydroxybenzoic acid (27.6 g), 4-chloro-3-cyanobenzotrifluoride (41.1 g) and anhydrous potassium carbonate (55.2 g) were stirred together for 7½ hours at 100° C. in dry dimethylformamide (500 ml) and then left at room temperature for 65 hours. The solvent was then removed under reduced pressure and the residue taken up in water and acidified with dilute hydrochloric acid. The solid which separated was washed with water, dissolved in ether and the solution dried and concentrated. The colourless solid which separated was recrystallized to give the benzoic acid derivative (24.0 g) with a melting point of 224°-226° C.

(b) Preparation of 5-(2-cyano-4-trifluoromethylphenoxy)-2-nitrobenzoic acid

The product from (a) (9.22 g) was added in portions to a mixture of 1,2-dichloroethane (25 ml) and concentrated sulphuric acid (40 ml) stirred at 0° C. Potassium nitrate (3.13 g) was then added in portions with stirring at 0° C., over a period of 15 minutes. The mixture was then stirred at 0° C. for 30 minutes, allowed to warm to room temperature, and poured into 200 ml of ice and water. The mixture was stirred until the ice had melted, and filtered with suction. The solid which separated on evaporation of the dichloroethane was washed with water and taken up in ether. The ether solution was treated with charcoal, dried and petroleum (b.p. 40°-60° C.) added. The solid which separated was identified as the required benzoic acid derivative (7.8 g) having a melting point of 190°-192° C.

EXAMPLE 8

This Example illustrates the preparation of 5-(2,4-dichlorophenoxy)-2-nitrobenzoic acid, useful as the starting material for the preparation of compound no 17 of Table 1.

The known compound methyl 2-nitro-5-(2,4-dichlorophenoxy)benzoate (55.0 g) was heated under reflux with 2 molar sodium hydroxide solution for 4 hours. The clear solution was cooled and acidified with hydrochloric acid. A yellow gum separated, which crystallised on stirring. The solid was recrystallised from toluene to give the required benzoic acid derivative (30.2 g), with a melting point of 167.5°-169.5° C.

EXAMPLE 9

This Example illustrates the preparation of 3(2,4-dichlorophenoxy)benzoic acid.

(a) Preparation of 3(2-chloro-4-nitrophenoxy)benzoic acid

A mixture of 3-hydroxybenzoic acid (5 g), dimethyl formamide (50 ml), 3,4-dichloronitrobenzene (7 g) and anhydrous potassium carbonate (10 g) was stirred and heated at 100° C. for 14 hours. The solvent was removed under reduced pressure and the residue poured into water and acidified with 2 molar hydrochloric acid. The yellow solid which separated was recrystallised from toluene to give the required benzoic acid derivative (8.0 g) with a melting point of 172°-173° C.

(b)

Concentrated hydrochloric acid (200 ml) was added dropwise to a mixture of 3(2-chloro-4-nitrophenoxy)benzoic acid (20 g) and granulated tin (40 g), the temperature being kept at 10°-15° C. When addition was complete, the mixture heated at 60° C. for 45 minutes, ethanol (100 ml) added, and the heating continued for another two hours. The mixture was allowed to cool, and the solid which separated was collected, dried, and extracted with hot methanol. Evaporation of the methanol extract gave the hydrochloride of 3(4-amino-2-chlorophenoxy)benzoic acid (19.5 g), with a melting point of 228°-232° C. (decomp).

(c)

The product (10 g) from paragraph (a) was dissolved in dimethyl formamide (150 ml), cooled to 5°-10° C. and concentrated hydrochloric acid (40 ml) added dropwise, the temperature being kept at 10°-15° C. The mixture was then kept at 5° C. while sodium nitrate (5.2 g) in water (20 ml) was added dropwise with stirring over a period of 30 minutes. The solution so prepared was added dropwise to a solution of cuprous chloride (19 g) in concentrated hydrochloric acid (150 ml) kept at 10° C., giving a thick green suspension. When addition was complete, the mixture was left to stand overnight and then heated to 60° C. for 30 minutes. The white solid was filtered off, dried, and recrystallised from petroleum (100°-120° C.) to give 3(2,4-dichlorophenoxy)benzoic acid (5.1 g) with a melting point of 143°-144° C. This compound was used as starting material for compound no 19 of Table 1.

EXAMPLE 10

This Example illustrates the preparation of 2-bromo-5-(2,4-dichlorophenoxy)benzoic acid useful as a starting material for compound no 20 of Table 1.

(a) Preparation of 2-amino-5-(2,4-dichlorophenoxy)benzoic acid hydrochloride.

Concentrated hydrochloric acid (100 ml) was added dropwise to a mixture of 5-(2,4-dichlorophenoxy)-2-nitrobenzoic acid (10 g) and granulated tin (20 g) cooled to 10°-15° C. The mixture was then heated to 60°-70° C. for 1 hour. Ethanol (100 ml) was added and the mixture heated for a further 2 hours at 60°-70° C. The precipitate was collected and recrystallised from ethanol to give the hydrochloride (3.8 g) with a melting point of 166°-168° C. with decomposition.

(b) Preparation of 2-bromo-5-(2,4-dichlorophenoxy)benzoic acid

The product from (a) above (3.8 g) dissolved in dimethyl formamide (100 ml) was cooled to 5° C. and concentrated hydrochloric acid (50 ml) added. The solution was kept at 5°-10° C. while sodium nitrite (2.0 g) in water (10 ml) was added dropwise with stirring. The solution so prepared was added dropwise to boiling hydrobromic acid (48%; 75 ml) containing cuprous bromide (7 g). When addition was complete the reaction was heated for another 15 minutes and then allowed to cool to room temperature. The mixture was diluted with water and extracted with ether. The ether extracts yielded an oil which solidified on standing and was recrystallised from petroleum (b.p. 100°-120° C.) to give the bromo-acid (1.0 g) with a melting point of 132°-133° C.

EXAMPLE 11

This Example illustrates the preparation of compound no 21 of Table 1.

(a) Preparation of ethyl 2-nitro-5-(2,4,6-trichlorophenoxy)benzoate.

2,4,6-Trichlorophenol (12.0 g) and anhydrous potassium carbonate (44 g) in dimethyl formamide (60 ml) were heated under reflux for 90 minutes and then left to cool overnight. Half of the dimethyl formamide was then distilled off. The remaining solution was cooled to 150°-160° C. and ethyl 5-chloro-2-nitrobenzoate (13.3 g) was added. The mixture was then heated under reflux for 8 hours. The dimethyl formamide was then removed under reduced pressure and the residue shaken with water (250 ml) and ether (250 ml). The ether layer was evaporated and washed with water and then dried and evaporated. The remaining oil was distilled and the fraction (9.9 g) boiling at 190°/0.1 Torr was collected and identified as the required ester.

(b) Preparation of 2-nitro-5-(2,4,6-trichlorophenoxy)benzoic acid

The product from paragraph (a) (6.86 g) in ethanol (50 ml) was heated and stirred with a solution of sodium hydroxide (0.8 g) in water (10 ml) at 60°-70° C. for 4 hours. The mixture was then cooled and the ethanol removed under reduced pressure. The residue was diluted to 100 ml with water and brought to pH2 with concentrated hydrochloric acid. The solid which separated was collected and recrystallised from toluene to give the required benzoic acid derivative (4.26 g) with a melting point of 192°-192.5° C.

(c) Preparation of compound no 21

The product from (b) above (1.5 g) was heated to reflux in thionyl chloride (10 ml) for 9 hours and the excess of thionyl chloride then removed under reduced pressure. The residue was taken up in pyridine (20 ml) and stirred with methanesulphonamide (0.7 g) for 7 hours and the solution then left to stand for two days. The pyridine was then removed under reduced pressure. The oil which remained was mixed with 2 molar hydrochloric acid (50 ml) and the solution extracted with ether (100 ml). The ether solution was washed with water (100 ml) and then dried and evaporated to give a solid which was recrystallised from toluene, to give 2-nitro-5-(2,4,6-trichlorophenoxy)-N-methanesulphonylbenzamide (1.05 g) with a melting point of 227.5° C.

EXAMPLE 12

This Example ilustrates the preparation of 2-nitro-5-(2,4,6-tribromophenoxy)benzoic acid, useful as starting material for the preparation of compound no 22 of Table 1.

(a) Preparation of ethyl 2-nitro-5-(2,4,6-tribromophenoxy)benzoate.

Ethyl 5-chloro-2-nitrobenzoate (10 g) and 2,4,6-tribromophenol (14.6 g) were heated and stirred with sodium carbonate (6.1 g) in dimethyl formamide at 130° C. for 17 hours. A further quantity of sodium carbonate (6.1 g) was then added and the mixture heated under reflux for another 38 hours. The solvent was removed under reduced pressure and the residue shaken with water and dichloromethane. The dichloromethane was dried and evaporated and the residue taken up in ether and the ether solution washed with water. The ether solution was dried and evaporated to leave an oil. This was distilled and the fraction (2.14 g) boiling at 202°–210° C./0.1 Torr collected.

(b) Preparation of 2-nitro-5-(2,4,6-tribromophenoxy)benzoic acid

The ester from (a) above (4.9 g) was stirred in ethanol (50 ml) with sodium hydroxide (0.4 g) dissolved in water (5 ml) at 60°–70° C. for 4 hours. The solvent was then removed under reduced pressure and the residue taken up in water and heated and stirred at 60° C. for five minutes. The solution was cooled and brought to pH2 with hydrochloric acid and extracted with ether (200 ml). The ether extracts yielded an oil which was dissolved in sodium carbonate solution and the solution extracted with dichloromethane. The aqueous solution was then acidified and extracted with ether. The ether extracts yielded an oil which was recrystallised from a mixture of toluene and petroleum, to give the acid (1.86 g) with a melting point of 162°–169.5° C.

EXAMPLE 13

This Example illustrates the preparation of N-methanesulphonyl 5-(2-fluoro-4-trifluoromethylphenoxy)-2-nitrobenzamide (Compound no. 38 of Table I).

(a) Preparation of methyl 5-(2-fluoro-4-trifluoromethylphenoxy)-2-nitrobenzoate.

3-Fluoro-4-hydroxybenzotrifluoride prepared as described in paragraph (c) of Example 16 (0.6 g) in diemthylsulphoxide (5 ml) was added in portions to a suspension of sodium hydride (50% oil dispersion, 0.16 g, petroleum washed) in dry dimethyl sulphoxide (10 ml) and the mixture stirred at room temperature for 30 minutes. A solution of 3-methoxycarbonyl-4-nitrofluorobenzene (0.66 g) in dimethylsulphoxide (5 ml) was then added. The mixture was stirred for 45 minutes and then heated at 100° for 90 minutes. The mixture was then cooled and poured into water (100 ml). The mixture was extracted with ether (150 ml) and the extract washed with water (100 ml), dried (MgSO4), and evaporated to give a yellow oil (0.8 g) which solidified. This was purified by thin layer chromatography on silica gel using a mixture of ether (1 volume) and petroleum (b.p. 60°–80°; 5 volumes) as eluent, to give a solid (0.5 g) identified as the required ester, with a melting point of 90.5° to 91.5° C.

(b) Preparation of compound 38

The ester from (b) was hydrolysed to the corresponding carboxylic acid by treatment with hydrobromic acid in aqueous acetic acid as described in paragraph (c) of Example 18. The carboxylic acid was then converted to the acid chloride and reacted with methanesulphonamide in the presence of caesium fluoride in butyl acetate, as described in paragraph (c) of Example 4.

EXAMPLE 14

This Example illustrates the preparation of N-methanesulphonyl-5-(2,4-bis-trifluoromethylphenoxy)-2-nitrobenzamide. (Compound 39 of Table I).

(a) Preparation of 5-(2,4-bis-trifluoromethylphenoxy)-benzoic acid 2,4-Bis-trifluoromethylbromobenzene (5.86 g prepared by treatment of 2,4-di-carboxybromobenzene with hydrogen fluoride and sulphur tetrafluoride), 3-hydroxybenzoic acid (2.76 g) and anhydrous potassium carbonate (5.52 g) were heated in dimethylsulphoxide (5 ml) to 125°–130° for 14 hours. The mixture was cooled and poured into ice and water (500 ml). The mixture was acidified (HCl) and extracted with ether (300 ml). The extract was washed with water (2×300 ml), dried (MgSO4), and evaporated to give a solid. Further solid was obtained by re-extraction of the aqueous fractions with ether (250 ml). The solids were combined, taken up in hot toluene (60 ml) and diluted with petroleum (b.p. 60°–80°) to precipitate 3-hydroxybenzoic acid. The mixture was filtered and the filtrate evaporated to give a solid. This was washed with petroleum (b.p. 30°–40°). The washings were evaporated to give more solid. The solids were combined and re-crystallised from petroleum (b.p. 80°–100°) to give the required carboxylic acid (0.5 g) having a melting point of 133°–134°.

(b) Preparation of 5-(2,4-bis-trifluoromethylphenoxy)-2-nitrobenzoic acid.

The carboxylic acid (1.05 g) prepared as described in (a) was added to 1,2-dichloroethane (5 ml) and concentrated sulphuric acid (5 ml) at 0°. The mixture was stirred and kept at 0°–5° while potassium nitrate (0.33 g) was added in portions over a period of 15 minutes.

The mixture was stirred at 0°–5° for a further 15 minutes, and poured on to ice and water (50 ml). The mixture was extracted with ether (2×150 ml) and the ether extract washed with water (50 ml), dried (MgSO4), and evaporated to give the nitro-acid (1.1 g).

(c) Preparation of compound 39

The product from (b) (1.0 g) was heated under reflux in thionyl chloride (20 ml) for 2 hours. The cooled solution was evaporated under reduced pressure to give an oil. This was taken up in dry butyl acetate (15 ml) and treated with methanesulphonamide (0.48 g) and dried caesium fluoride (1.0 g). The mixture was stirred and heated under reflux for 3 hours. The cooled mixture was diluted with water and acidified with dilute hydrochloric acid.

The mixture was extracted with ethyl acetate (2×30 ml). The extract was washed with water (2×50 ml) and dried (MgSO₄). Removal of the ethyl acetate gave a solid which was triturated with ether (30 ml). The ether solution so obtained was diluted with petroleum (b.p. 30°-40°). The solid which separated (0.5 g) was identified as compound no. 39, with a melting point of 170°-171° after re-crystallisation from isopropanol.

EXAMPLE 15

This Example illustrates the preparation of N-methane-sulphonyl-5-(2,6-dichloro-4-trifluoromethylphenoxy)-2-nitrobenzamide (compound 42 of Table I).
(a) Preparation of 3,5-dichloro-4-fluorobenzotrifluoride 2,6-Dichloro-4-trifluoromethylaniline (6.5 g) in concentrated hydrochloric acid (18 ml) was cooled to 0° C. Sodium nitrite (1.95 g) dissolved in a little water was added slowly while the solution was stirred and kept below 5° C. When addition was complete the solution was stirred for 1 hour, filtered, and added to a solution of sodium fluoroborate (6 g) in water (10 ml). The precipitate was washed with a little cold water and with ether, and dried. The solid was heated with the flame of a Bunsen burner until decomposition took place; the product distilled from the reaction flask and was collected, taken up in ether, and washed with water. The ether solution was dried and evaporated to give an oil, which was distilled under reduced pressure to give the benzotrifluoride derivative (1.5 g).
(b) Preparation of 3-(2,6-dichloro-4-trifluoromethylphenoxy)benzoic acid.

The product from (a) (1.5 g) was heated with 3-hydroxybenzoic acid (0.95 g) and anhydrous potassium carbonate (0.95 g) in dimethyl sulphoxide (20 ml) at 100° C. for 2 hours. The mixture was diluted with water and the resulting precipitate (1.5 g) collected, dried, and identified as the substituted benzoic acid, having a melting point of 204° C. (melts and resolidifies at 150° C.).
(c) Preparation of 5-(2,6-dichloro-4-trifluoromethylphenoxy)-2-nitrobenzoic acid.

The product from (b) (1.4 g) in 1,2-dichloroethane (10 ml) was cooled to 0° C. and mixed with concentrated sulphuric acid (5 ml). The mixture was stirred while potassium nitrate (0.4 g) was added in portions over a period of 30 minutes. The mixture was then stirred at room temperature for 30 minutes, and then agitated with chloroform and water. The chloroform layer was washed with water, dried (MgSO₄), and evaporated to give a yellow oil (1.05 g) which solidified and was identified as the required substituted benzoic acid. After recrystallisation from a mixture of chloroform and hexane, the compound had a melting point of 162°-163°.
(d) Preparation of N-methanesulphonyl 5-(2,6-dichloro-4-trifluoromethylphenoxy)-2-nitro benzamide (Compound 42)

The acid prepared according to (c) above was converted to its acid chloride by treatment with thionyl chloride as described in Example 20.

The acid chloride (0.73 g) so obtained was taken up in pyridine (10 ml) and cooled to 0° C.

Methanesulphonamide (0.3 g) was added and the solution stirred at 0° C. for 1 hour and room temperature for 2 hours. The excess of pyridine was removed under reduced pressure and the residue treated with dilute hydrochloric acid. The buff solid so obtained was purified by thin-layer chromatography on silica gel using ethyl acetate containing 5% methanol as the eluent. The sulphonamide (compound 42) had a melting point of 242°-243° C.

The 2,6-dichloro-4-trifluoromethylaniline required for stage (a) of the above process was prepared as follows:

Chlorine was passed into a solution of p-trifluoromethylaniline (3.46 kg) in glacial acetic acid (7 liters). After 90 minutes the temperature had reached 60° and a solid was separating. Chlorination was continued for 13.5 hours, keeping the temperature between 60° and 90° with occasional warming. The suspension was filtered and the residue washed with 1 liter of cold acetic acid. The residue was then twice stirred with water (8 liters) and sucked dry on the filter to give the required dichloro compound.

EXAMPLE 16

This Example illustrates the preparation of N-methanesulphonyl-5-(2-chloro-6-fluoro-4-trifluoromethylphenoxy)-2-nitrobenzamide. (Compound no. 44 of Table I).
(a) Preparation of 4-methoxy-3-nitro-benzotrifluoride 4-chloro-3-nitrobenzotrifluoride (112.8 g) in methanol (200 ml) was mixed with a solution of sodium (11.6 g) in methanol (800 ml) and stirred for 2 hours. The mixture was kept overnight and then stirred and heated under reflux for 3 hours. The solution was left overnight, filtered, and the solvent removed. The remaining oil was taken up in ether (500 ml) and washed with water.

The ether solution was dried and evaporated to give 4-methoxy-3-nitrobenzotrifluoride (106 g).
(b) Preparation of 3-amino-4-methoxy benzotrifluoride 4-Methoxy-3-nitrobenzotrifluoride (95 g) in isopropanol (1.0 liter) and water (250 ml) was mixed with concentrated hydrochloric acid (15 ml). Iron powder (180 g) was added and the mixture was heated and stirred under reflux. After 90 minutes the mixture was cooled to 50° C. and filtered. The residue was washed with isopropanol and the combined filtrates evaporated. The residue was dissolved in toluene and the solution dried (MgSO₄) and evaporated. The residue was triturated with light petroleum (b.p. 30°-40°) to give the 3-amino-4-methoxybenzotrifluoride as a colourless solid (68 g).
(c) Preparation of 3-fluoro-4-methoxybenzotrifluoride The product from (b) (57.3 g) was added to concentrated hydrochloric acid (220 ml). The mixture was stirred vigorously and kept at 0°-5° C. while a solution of sodium nitrite (24 g) in water (40 ml) was added dropwise. The solution was stirred for a further 30 minutes, filtered at 0°-5° C., and poured into a solution of sodium fluoroborate (80 g) in water (100 ml) with stirring. The mixture was cooled in ice/salt and filtered. The residue was washed with dilute sodium fluoroborate, a little cold ethanol, and ether, to give the diazonium fluoroborate (70 g). This material (10 g) was heated gently with the flame of a Bunsen burner until decomposition occurred. The product distilled from the reaction flask and was collected. The combined product from seven such decompositions (about 35 g) was distilled to give 3-fluoro-4-methoxybenzotrifluoride (32 g) with a boiling point of 87°-90°/30 Torr.
(d) Preparation of 3-fluoro-4-hydroxybenzotrifluoride The product from (c) (5 g) was fused with pyridine hydrochloride (25 g) at 195°-200° C. for 210 minutes. The cooled reaction mixture was agitated with ether (150 ml) and water (100 ml). The mixture was acidified (HCl) and the ether layer separated and washed successively with water, sodium bicarbonate solution, and water, and then dried and evaporated to leave a colourless oil (4.2 g) identified as 3-fluoro-4-hydroxybenzotrifluoride.

(e) Preparation of 3-fluoro-4-hydroxy-5-nitro-benzotrifluoride

The product from (c) (4.1 g) in 1,2-dichloro-ethane (25 ml) was chilled to −10° C. and concentrated sulphuric acid (25 ml) added. The mixture was stirred and kept at −5° to −10° C. while potassium nitrate (2.3 g) was added in portions over a period of 30 minutes. The mixture was stirred for a further 30 minutes at below 0° C. and then poured on to ice (150 ml). The mixture was extracted with chloroform (150 ml) and the extracts washed with water (100 ml), dried (MgSO$_4$) and evaporated to give 3-fluoro-4-hydroxy-5-nitrobenzotrifluoride as a pale yellow liquid (4.1 g).

(f) Preparation of 3-amino-5-fluoro-4-hydroxy-benzotrifluoride

The product from (e) (4.1 g) in water (50 ml) was stirred vigorously while sodium dithionite hydrate (10 g) was added in portions. The mixture was stirred for 30 minutes and then ethanol (25 ml) and further sodium dithionite (5 g) were added. The mixture was stirred for another 15 minutes and then diluted to 400 ml, acidified (HCl) and extracted with dichloromethane (4×200 ml). The dichloromethane extract was dried (MgSO$_4$) and evaporated to give a yellow oil which crystallised on cooling. This was identified as 3-amino-5-fluoro-4-hydroxybenzotrifluoride (2.9 g).

(g) Preparation of 3-fluoro-2(3-methoxycarbonyl-4-nitrophenoxy)-4-trifluoromethyl aniline.

The product prepared as described in (f) (8.9 g) was heated and stirred under reflux in methyl ethyl ketone with anhydrous potassium carbonate (10.0 g) and 3-methoxycarbonyl-4-nitro-fluoro-benzene (10.0 g) for 4.5 hours. The mixture was filtered and the filtrate evaporated. The remaining brown solid was recrystallised from ethanol (75 ml) to give a pale yellow solid (12.5 g) having a melting point of 138°-139°, identified as the required aniline derivative.

(h) Preparation of 3-fluoro-2(3-methoxycarbonyl-4-nitrophenoxy)-5-trifluoromethylbenzenediazonium fluoroborate.

The product from (g) (12 g) in trifluoroacetic acid (30 ml) was diluted with 40% aqueous fluoroboric acid (30 ml). The solution was cooled to 0° C. and treated dropwise with stirring with a solution of sodium nitrite (2.45 g) in water (6 ml) over a period of 75 minutes, keeping the solution at about 3° C. during the addition. The reaction mixture was then cooled to 0° C. and kept at 0°-5° C. for 1 hour. Further fluoroboric acid (20 ml) was added and the mixture kept at 0° C. for another 30 minutes. The mixture was then filtered and the solid washed with a little cold ethanol, and then with ether, giving the required diazonium fluoroborate (14.4 g).

(i) Preparation of methyl 5(2-chloro-6-fluoro-4-trifluoromethylphenoxy)-2-nitrobenzoate.

The product from (h) (7.0 g) was finely powdered and added in portions over a period of 15 minutes to a solution of cuprous chloride (anhydrous; 4.06 g) in dry dimethyl sulphoxide (60 ml). The mixture was stirred for a further 30 minutes, poured into a mixture of water and ice (300 ml) and extracted with ether (3×100 ml). The ether extract was washed with water (2×100 ml), dried (MgSO$_4$) and evaporated to give an oil, which solidified.

This material was purified by thin layer chromatography on silica gel using a mixture of ether (1 volume) and petroleum (bp. 60°-80° C.; 3 volumes) as the eluent. The product so obtained (2.9 g) had a melting point of 79°-80° C. and was identified as the required methyl 5-(2-chloro-6-fluoro-4-trifluoromethylphenoxy)-2-nitrobenzoate.

(j) Preparation of N-methanesulphonyl 5-(2-chloro-6-fluoro-4-trifluoromethylphenoxy)-2-nitrobenzamide (compound no 44).

The ester prepared in (i) was hydrolysed to the corresponding carboxylic acid by treatment with hydrogen bromide in acetic acid following the procedure described in paragraph (c) of Example 18. The carboxylic acid (melting point 145-1481) was identified as 5-(2-chloro-6-fluoro-4-trifluoromethylphenoxy)-2-nitrobenzoic acid by its elemental analysis and spectral properties. The carboxylic acid so prepared (2 g) was heated under reflux in thionyl chloride (30 ml) for 2 hours. The excess thionyl chloride was removed under reduced pressure and the residue taken up in butyl acetate (30 ml) and stirred and heated under reflux with dry caesium fluoride (3.0 g) and methane-sulphonamide (1 g) for 2 hours). The solution was cooled, diluted with water (250 ml), and acidified (HCl). The mixture was extracted with ethyl acetate (300 ml). The extract was washed with water, dried (MgSO$_4$) and evaporated to give an oil. Toluene was added and evaporated under reduced pressure. The remaining solid was recrystallised from isopropanol (10 ml). The recrystallised solid was washed with a little isopropanol and then light petroleum (bp. 30°-40°) to give the required benzamide derivative (compound 44) as colourless crystals (1.6 g) with a melting point of 171°-172°.

Further esters of 5-(2-chloro-6-fluoro-5-trifluoromethylphenoxy)-2-nitrobenzoic acid were prepared as follows:

5-(2-Chloro-6-fluoro-4-trifluoromethylphenoxy)-2-nitrobenzoic acid (2.5 g) was heated under reflux for 5 hours with thionyl chloride (40 ml). The solution was evaporated under reduced pressure and the yellow oil remaining was taken up in toluene (100 ml). The solution was divided into four portions. Each portion was separately evaporated to give 5-(2-chloro-6-fluoro-4-trifluoromethylphenoxy)-2-nitrobenzoyl chloride as an oil. Three portions were used to prepare esters as follows:

(1) Ethyl ester.

The acid chloride (0.5 g) was cooled in ice and stirred with ethanol (15 ml). The yellow solution so obtained was left for 48 hours at room temperature and then evaporated to give an oil. This was purified by thin-layer chromatography (silica gel as solid phase, ether as the solvent). The ester travelled near the solvent front and was readily separated from the carboxylic acid present as impurity. The ester was extracted with ethyl acetate. The extract was evaporated to give a colourless oil (0.3 g) which slowly crystallised to give solid ethyl (5-(2-chloro-6-fluoro-4-trifluoromethylphenoxy)-2-nitro benzoate with a melting point of 52°-53°. (Found: C 47.16; H 2.64; N 3.46%; $C_{16}H_{10}ClF_4NO_5$ requires C 47.13; H 2.47; N 3.44%). The NMR and mass spectrum confirmed the identity of the product; traces of the 2,6-dichloro analogue and an isomer differing in the position of the nitro group were also present.

(2) Propyl ester.

The propyl ester was prepared in a similar way to the ethyl ester using n-propanol. The NMR and mass spectrum confirmed the identity of the product, which was a yellow oil. (Found: C 48.61; H 2.87; N 3.81%; $C_{17}H_{12}ClF_4NO_5$ requires C 48.4; H 2.87; N 3.32%).

(3) Butyl ester.

The butyl ester was prepared as described for the ethyl ester, using n-butanol instead of ethanol. Purification was by thin layer chromatography (solid phase silica gel) first with ether as solvent and then with cyclohexane/chloroform/methanol (50:50:5). The product was a yellow oil. The structure was confirmed by the NMR and mass spectrum, and the elemental analysis (Found: C 49.42; H 3.23; N 3.45% $C_{18}H_{14}ClF_4NO_5$ requires C 49.61; H 3.24; N 3.22%).

EXAMPLE 17

This Example illustrates the preparation of N-methanesulphonyl 5-(2,6-difluoro-4-trifluoromethylphenoxy)-2-nitrobenzamide (compound 48 of Table I).

(a) Preparation of methyl 5-(2,6-difluoro-4-trifluoromethylphenoxy)-2-nitro benzoate.

The diazonium fluoroborate prepared as described in paragraph (h) of Example 16 (7.0 g) was suspended in carbon tetrachloride (400 ml). Aqueous fluoroboric acid (40%; 200 ml) was added and the mixture was stirred while being irradiated by an internally placed medium pressure mercury vapour lamp for 6 hours. Further amounts of carbon tetrachloride (100 ml) and fluoroboric acid (100 ml) were then added and the mixture flushed continuously with a stream of nitrogen to aid mixing. After 4 hours the solid was filtered off. The solid and the aqueous fluoroboric acid was returned to the reaction flask and the carbon tetrachloride washed with water (2×500 ml), dried, and evaporated to give a solid (2.1 g). Fresh carbon tetrachloride was added to the reaction flask and stirring and irradiation continued for another 8 hours. The carbon tetrachloride layer was separated, washed with water and dried. Evaporation of the carbon tetrachloride gave a solid (2.3 g) which was combined with the solid obtained earlier, and purified by thin layer chromatography on silica gel, using a mixture of ether (1 volume) and petroleum (b.p. 60°-80° C.; 3 volumes) as the eluent. The major component was extracted with ether (ca. 1 liter). Evaporation of the ether gave a solid (2.55 g) which was found to contain 85% of the required methyl 5-(2,6-difluoro-4-trifluoromethylphenoxy)-2-nitrobenzoate upon examination by nuclear magnetic resonance spectroscopy.

(b) Preparation of 5-(2,6-difluoro-4-trifluoromethylphenoxy)-2-nitrobenzoic acid.

The product from paragraph (a) (2.4 g) in acetic acid (60 ml) was mixed with hydrobromic acid (40%; 35 ml) and stirred and heated under reflux for 6.5 hours. The solution was evaporated under reduced pressure and the residue re-evaporated with toluene (2×100 ml) to remove traces of water and acetic acid. The oil so obtained was taken up in a little ether and filtered. The filtrate was diluted with petroleum (b.p. 40°-60° C.; 200 ml) and again filtered. A solid (1.49 g) slowly crystallised from the filtrate. The solid was recrystallised from toluene. Thin layer chromatography showed that the recrystallised solid contained two components. This solid, and a further solid obtained by evaporating the toluene used for recrystallising it, were separately purified by thin layer chromatography on silica gel using a mixture of ethyl acetate, acetic acid, and water (250:5:1) as the solvent. The major component was extracted from the thin layer plates with ethanol. The solid so obtained was treated with 2-molar hydrochloric acid and extracted with ethyl acetate. The extract was dried and evaporated to give a solid. This was re-evaporated with toluene to give a solid (1.2 g) identified as 5-(2,6-difluoro-4-trifluoromethylphenoxy)-2-nitrobenzoic acid, having a melting point of 149°-150° C.

(c) Preparation of N-methanesulphonyl-5-(2,6-difluoro-4-trifluoromethylphenoxy)-2-nitrobenzamide The carboxylic acid from (b) (1.41 g) was heated under reflux for 2 hours in thionyl chloride (20 ml). The excess of thionyl chloride was removed under reduced pressure. The treatment with thionyl chloride was repeated and the excess again removed. The remaining solid was taken up in dry butyl acetate (15 ml) and heated under reflux with caesium fluoride (2.1 g) and methanesulphonamide (0 6 g) for 75 minutes. The mixture was cooled, diluted with ethyl acetate (150 ml) and water (75 ml), and acidified (HCl). The organic layer was separated, washed with water (100 ml), dried ($MgSO_4$), and evaporated. Toluene was added to the residue and evaporated under reduced pressure. The remaining solid was recrystallised from isopropanol to give a colourless solid (0.838 g) having a melting point of 204°-205° identified as the required compound 48.

Further esters of 5-(2,6-difluoro-4-trifluoromethylphenoxy)-2-nitrobenzoic acid were prepared as follows:

5-(2,6-Difluoro-4-trifluoromethylphenoxy)-2-nitrobenzoic acid (ca. 1 g) was heated under reflux with thionyl chloride (20 ml) for 3 hours. The thionyl chloride was removed and the residue diluted with dry toluene. The solution was divided into four. Each portion was evaporated and treated respectively with methanol, ethanol, n-propanol, and n-butanol, as described in Example 16 for the preparation of esters of 5-(2-chloro-6-fluoro-4-trifluoromethylphenoxy)-2-nitrobenzoic acid. Details of the esters so prepared are given below:

Methyl ester

Melting point 99°-100°. Structure confirmed by NMR, mass spectrum, and elemental analysis (Found: C 47.72; H 2.23; N 3.73% $C_{15}H_8F_5NO_5$ requires C 47.76; H 2.14; N 3.71%).

Ethyl ester

Oil. Structure confirmed by NMR, mass spectrum, and elemental analysis. (Found: C 49.10; H 2.54; N 3.60%. $C_{16}H_{10}F_5NO_5$ requires C 49.11; H 2.58; N 3.58%).

Propyl ester

Oil. Structure confirmed by NMR, mass spectrum, and elemental analysis. (Found: C 50.42; H 2.95; N 3.44%. $C_{17}H_{12}F_5NO_5$ requires C 50.38; H 2.99; N 3.46%).

Butyl ester

Oil. Structure confirmed by NMR, mass spectrum, and elemental analysis. (Found: C 51.39; H 3.14; N 3.32%. $C_{18}H_{14}F_5NO_5$ requires C 51.56; H 3.37; N 3.34%).

EXAMPLE 18

This Example illustrates the preparation of N-methanesulphonyl 5-(2-methyl-4-trifluoromethylphenoxy)-2-nitrobenzamide (compound 49 of Table I).

(a) Preparation of 4-hydroxy-3-methylbenzotrifluoride.

3-Methyl-4-nitrobenzoic acid was converted to 3-methyl-4-nitrobenzotrifluoride by treatment with sulphur tetrafluoride and hydrogen fluoride. The 3-methyl-4-nitrobenzotrifluoride so prepared was reduced to 4-amino-3-methylbenzotrifluoride. This was diazotised in the usual way (e.g. as in paragraph (a) of Example 15)

sively with water, sodium bicarbonate solution, and water, and then dried and evaporated to leave a colourless oil (4.2 g) identified as 3-fluoro-4-hydroxybenzotrifluoride.

(e) Preparation of 3-fluoro-4-hydroxy-5-nitro-benzotrifluoride

The product from (c) (4.1 g) in 1,2-dichloro-ethane (25 ml) was chilled to $-10°$ C. and concentrated sulphuric acid (25 ml) added. The mixture was stirred and kept at $-5°$ to $-10°$ C. while potassium nitrate (2.3 g) was added in portions over a period of 30 minutes. The mixture was stirred for a further 30 minutes at below $0°$ C. and then poured on to ice (150 ml). The mixture was extracted with chloroform (150 ml) and the extracts washed with water (100 ml), dried ($MgSO_4$) and evaporated to give 3-fluoro-4-hydroxy-5-nitrobenzotrifluoride as a pale yellow liquid (4.1 g).

(f) Preparation of 3-amino-5-fluoro-4-hydroxy-benzotrifluoride

The product from (e) (4.1 g) in water (50 ml) was stirred vigorously while sodium dithionite hydrate (10 g) was added in portions. The mixture was stirred for 30 minutes and then ethanol (25 ml) and further sodium dithionite (5 g) were added. The mixture was stirred for another 15 minutes and then diluted to 400 ml, acidified (HCl) and extracted with dichloromethane ($4 \times 200$ ml). The dichloromethane extract was dried ($MgSO_4$) and evaporated to give a yellow oil which crystallised on cooling. This was identified as 3-amino-5-fluoro-4-hydroxybenzotrifluoride (2.9 g).

(g) Preparation of 3-fluoro-2(3-methoxycarbonyl-4-nitrophenoxy)-4-trifluoromethyl aniline.

The product prepared as described in (f) (8.9 g) was heated and stirred under reflux in methyl ethyl ketone with anhydrous potassium carbonate (10.0 g) and 3-methoxycarbonyl-4-nitro-fluoro-benzene (10.0 g) for 4.5 hours. The mixture was filtered and the filtrate evaporated. The remaining brown solid was recrystallised from ethanol (75 ml) to give a pale yellow solid (12.5 g) having a melting point of $138°-139°$, identified as the required aniline derivative.

(h) Preparation of 3-fluoro-2(3-methoxycarbonyl-4-nitrophenoxy)-5-trifluoromethylbenzenediazonium fluoroborate.

The product from (g) (12 g) in trifluoroacetic acid (30 ml) was diluted with 40% aqueous fluoroboric acid (30 ml). The solution was cooled to $0°$ C. and treated dropwise with stirring with a solution of sodium nitrite (2.45 g) in water (6 ml) over a period of 75 minutes, keeping the solution at about $3°$ C. during the addition. The reaction mixture was then cooled to $0°$ C. and kept at $0°-5°$ C. for 1 hour. Further fluoroboric acid (20 ml) was added and the mixture kept at $0°$ C. for another 30 minutes. The mixture was then filtered and the solid washed with a little cold ethanol, and then with ether, giving the required diazonium fluoroborate (14.4 g).

(i) Preparation of methyl 5(2-chloro-6-fluoro-4-trifluoromethylphenoxy)-2-nitrobenzoate.

The product from (h) (7.0 g) was finely powdered and added in portions over a period of 15 minutes to a solution of cuprous chloride (anhydrous; 4.06 g) in dry dimethyl sulphoxide (60 ml). The mixture was stirred for a further 30 minutes, poured into a mixture of water and ice (300 ml) and extracted with ether ($3 \times 100$ ml). The ether extract was washed with water ($2 \times 100$ ml), dried ($MgSO_4$) and evaporated to give an oil, which solidified.

This material was purified by thin layer chromatography on silica gel using a mixture of ether (1 volume) and petroleum (bp. $60°-80°$ C.; 3 volumes) as the eluent. The product so obtained (2.9 g) had a melting point of $79°-80°$ C. and was identified as the required methyl 5(2-chloro-6-fluoro-4-trifluoromethylphenoxy)-2-nitrobenzoate.

(j) Preparation of N-methanesulphonyl 5-(2-chloro-6-fluoro-4-trifluoromethylphenoxy)-2-nitrobenzamide (compound no 44).

The ester prepared in (i) was hydrolysed to the corresponding carboxylic acid by treatment with hydrogen bromide in acetic acid following the procedure described in paragraph (c) of Example 18. The carboxylic acid (melting point 145-148l) was identified as 5-(2-chloro-6-fluoro-4-trifluoromethylphenoxy)-2-nitrobenzoic acid by its elemental analysis and spectral properties. The carboxylic acid so prepared (2 g) was heated under reflux in thionyl chloride (30 ml) for 2 hours. The excess thionyl chloride was removed under reduced pressure and the residue taken up in butyl acetate (30 ml) and stirred and heated under reflux with dry caesium fluoride (3.0 g) and methane-sulphonamide (1 g) for 2 hours). The solution was cooled, diluted with water (250 ml), and acidified (HCl). The mixture was extracted with ethyl acetate (300 ml). The extract was washed with water, dried ($MgSO_4$) and evaporated to give an oil. Toluene was added and evaporated under reduced pressure. The remaining solid was recrystallised from isopropanol (10 ml). The recrystallised solid was washed with a little isopropanol and then light petroleum (bp. $30°-40°$) to give the required benzamide derivative (compound 44) as colourless crystals (1.6 g) with a melting point of $171°-172°$.

Further esters of 5-(2-chloro-6-fluoro-5-trifluoromethylphenoxy)-2-nitrobenzoic acid were prepared as follows:

5-(2-Chloro-6-fluoro-4-trifluoromethylphenoxy)-2-nitrobenzoic acid (2.5 g) was heated under reflux for 5 hours with thionyl chloride (40 ml). The solution was evaporated under reduced pressure and the yellow oil remaining was taken up in toluene (100 ml). The solution was divided into four portions. Each portion was separately evaporated to give 5-(2-chloro-6-fluoro-4-trifluoromethylphenoxy)-2-nitrobenzoyl chloride as an oil. Three portions were used to prepare esters as follows:

(1) Ethyl ester.

The acid chloride (0.5 g) was cooled in ice and stirred with ethanol (15 ml). The yellow solution so obtained was left for 48 hours at room temperature and then evaporated to give an oil. This was purified by thin-layer chromatography (silica gel as solid phase, ether as the solvent). The ester travelled near the solvent front and was readily separated from the carboxylic acid present as impurity. The ester was extracted with ethyl acetate. The extract was evaporated to give a colourless oil (0.3 g) which slowly crystallised to give solid ethyl (5-(2-chloro-6-fluoro-4-trifluoromethylphenoxy)-2-nitro benzoate with a melting point of $52°-53°$. (Found: C 47.16; H 2.64; N 3.46%; $C_{16}H_{10}ClF_4NO_5$ requires C 47.13; H 2.47; N 3.44%). The NMR and mass spectrum confirmed the identity of the product; traces of the 2,6-dichloro analogue and an isomer differing in the position of the nitro group were also present.

(2) Propyl ester.

The propyl ester was prepared in a similar way to the ethyl ester using n-propanol. The NMR and mass spectrum confirmed the identity of the product, which was a yellow oil. (Found: C 48.61; H 2.87; N 3.81%; $C_{17}H_{12}ClF_4NO_5$ requires C 48.4; H 2.87; N 3.32%).

(3) Butyl ester.

The butyl ester was prepared as described for the ethyl ester, using n-butanol instead of ethanol. Purification was by thin layer chromatography (solid phase silica gel) first with ether as solvent and then with cyclohexane/chloroform/methanol (50:50:5). The product was a yellow oil. The structure was confirmed by the NMR and mass spectrum, and the elemental analysis (Found: C 49.42; H 3.23; N 3.45% $C_{18}H_{14}ClF_4NO_5$ requires C 49.61; H 3.24; N 3.22%).

EXAMPLE 17

This Example illustrates the preparation of N-methanesulphonyl 5-(2,6-difluoro-4-trifluoromethylphenoxy)-2-nitrobenzamide (compound 48 of Table I).

(a) Preparation of methyl 5-(2,6-difluoro-4-trifluoromethylphenoxy)-2-nitro benzoate.

The diazonium fluoroborate prepared as described in paragraph (h) of Example 16 (7.0 g) was suspended in carbon tetrachloride (400 ml). Aqueous fluoroboric acid (40%; 200 ml) was added and the mixture was stirred while being irradiated by an internally placed medium pressure mercury vapour lamp for 6 hours. Further amounts of carbon tetrachloride (100 ml) and fluoroboric acid (100 ml) were then added and the mixture flushed continuously with a stream of nitrogen to aid mixing. After 4 hours the solid was filtered off. The solid and the aqueous fluoroboric acid was returned to the reaction flask and the carbon tetrachloride washed with water (2×500 ml), dried, and evaporated to give a solid (2.1 g). Fresh carbon tetrachloride was added to the reaction flask and stirring and irradiation continued for another 8 hours. The carbon tetrachloride layer was separated, washed with water and dried. Evaporation of the carbon tetrachloride gave a solid (2.3 g) which was combined with the solid obtained earlier, and purified by thin layer chromatography on silica gel, using a mixture of ether (1 volume) and petroleum (b.p. 60°-80° C.; 3 volumes) as the eluent. The major component was extracted with ether (ca. 1 liter). Evaporation of the ether gave a solid (2.55 g) which was found to contain 85% of the required methyl 5-(2,6-difluoro-4-trifluoromethylphenoxy)-2-nitrobenzoate upon examination by nuclear magnetic resonance spectroscopy.

(b) Preparation of 5-(2,6-difluoro-4-trifluoromethylphenoxy)-2-nitrobenzoic acid.

The product from paragraph (a) (2.4 g) in acetic acid (60 ml) was mixed with hydrobromic acid (40%; 35 ml) and stirred and heated under reflux for 6.5 hours. The solution was evaporated under reduced pressure and the residue re-evaporated with toluene (2×100 ml) to remove traces of water and acetic acid. The oil so obtained was taken up in a little ether and filtered. The filtrate was diluted with petroleum (b.p. 40°-60° C.; 200 ml) and again filtered. A solid (1.49 g) slowly crystallised from the filtrate. The solid was recrystallised from toluene. Thin layer chromatography showed that the recrystallised solid contained two components. This solid, and a further solid obtained by evaporating the toluene used for recrystallising it, were separately purified by thin layer chromatography on silica gel using a mixture of ethyl acetate, acetic acid, and water (250:5:1) as the solvent. The major component was extracted from the thin layer plates with ethanol. The solid so obtained was treated with 2-molar hydrochloric acid and extracted with ethyl acetate. The extract was dried and evaporated to give a solid. This was re-evaporated with toluene to give a solid (1.2 g) identified as 5-(2,6-difluoro-4-trifluoromethylphenoxy)-2-nitrobenzoic acid, having a melting point of 149°-150° C.

(c) Preparation of N-methanesulphonyl-5-(2,6-difluoro-4-trifluoromethylphenoxy)-2-nitrobenzamide The carboxylic acid from (b) (1.41 g) was heated under reflux for 2 hours in thionyl chloride (20 ml). The excess of thionyl chloride was removed under reduced pressure. The treatment with thionyl chloride was repeated and the excess again removed. The remaining solid was taken up in dry butyl acetate (15 ml) and heated under reflux with caesium fluoride (2.1 g) and methanesulphonamide (0 6 g) for 75 minutes. The mixture was cooled, diluted with ethyl acetate (150 ml) and water (75 ml), and acidified (HCl). The organic layer was separated, washed with water (100 ml), dried (MgSO₄), and evaporated. Toluene was added to the residue and evaporated under reduced pressure. The remaining solid was recrystallised from isopropanol to give a colourless solid (0.838 g) having a melting point of 204°-205° identified as the required compound 48.

Further esters of 5-(2,6-difluoro-4-trifluoromethylphenoxy)-2-nitrobenzoic acid were prepared as follows:

5-(2,6-Difluoro-4-trifluoromethylphenoxy)-2-nitrobenzoic acid (ca. 1 g) was heated under reflux with thionyl chloride (20 ml) for 3 hours. The thionyl chloride was removed and the residue diluted with dry toluene. The solution was divided into four. Each portion was evaporated and treated respectively with methanol, ethanol, n-propanol, and n-butanol, as described in Example 16 for the preparation of esters of 5-(2-chloro-6-fluoro-4-trifluoromethylphenoxy)-2-nitrobenzoic acid. Details of the esters so prepared are given below:

Methyl ester

Melting point 99°-100°. Structure confirmed by NMR, mass spectrum, and elemental analysis (Found: C 47.72; H 2.23; N 3.73% $C_{15}H_8F_5NO_5$ requires C 47.76; H 2.14; N 3.71%).

Ethyl ester

Oil. Structure confirmed by NMR, mass spectrum, and elemental analysis. (Found: C 49.10; H 2.54; N 3.60%. $C_{16}H_{10}F_5NO_5$ requires C 49.11; H 2.58; N 3.58%).

Propyl ester

Oil. Structure confirmed by NMR, mass spectrum, and elemental analysis. (Found: C 50.42; H 2.95; N 3.44%. $C_{17}H_{12}F_5NO_5$ requires C 50.38; H 2.99; N 3.46%).

Butyl ester

Oil. Structure confirmed by NMR, mass spectrum, and elemental analysis. (Found: C 51.39; H 3.14; N 3.32%. $C_{18}H_{14}F_5NO_5$ requires C 51.56; H 3.37; N 3.34%).

EXAMPLE 18

This Example illustrates the preparation of N-methanesulphonyl 5-(2-methyl-4-trifluoromethylphenoxy)-2-nitrobenzamide (compound 49 of Table I).

(a) Preparation of 4-hydroxy-3-methylbenzotrifluoride.

3-Methyl-4-nitrobenzoic acid was converted to 3-methyl-4-nitrobenzotrifluoride by treatment with sulphur tetrafluoride and hydrogen fluoride. The 3-methyl-4-nitrobenzotrifluoride so prepared was reduced to 4-amino-3-methylbenzotrifluoride. This was diazotised in the usual way (e.g. as in paragraph (a) of Example 15)

and the diazonium salt isolated as its fluoroborate. The 2-methyl-4-trifluoromethylbenzenediazonium fluoroborate so prepared (6.0 g) in dilute (2.5M) sulphuric acid (150 ml) was heated to 80° over a period of 10 minutes. The solution was then cooled by adding ice, and extracted with dichloromethane (2×100 ml). The extract was dried (MgSO$_4$) and evaporated to give the phenol as a brown liquid.

(b) Preparation of methyl 5(2-methyl-4-trifluoromethylphenoxy)-2-nitrobenzoate.

The phenol prepared in (a) (3.52 g) was stirred and heated under reflux with 3-methoxycarbonyl-4-nitrofluorobenzene (4.0 g) and anhydrous potassium carbonate (3.0 g) in dry methyl ethyl ketone (50 ml) for 6.5 hours. The mixture was cooled, left overnight, and filtered. The filtrate was evaporated and the residue extracted with petroleum (b.p. 40°-60°; 150 ml) and ether (10 ml). The extract was filtered and evaporated to give the required ester as a viscous oil (6.6 g).

(c) Preparation of 5-(2-methyl-4-trifluoromethylphenoxy)-2-nitrobenzoic acid

The product from (b) (6.6 g) in acetic acid (100 ml) was mixed with 48% aqueous hydrobromic acid (65 ml). The mixture was stirred and heated under reflux for 7 hours. The solution was cooled and left for 48 hours. The solvents were removed and the residue mixed with toluene (200 ml). The toluene was evaporated off and the remaining solid dissolved in a little ether and the solution filtered. The ether solution was diluted with petroleum (b.p. 40-60; 200 ml), quickly filtered, and allowed to stand. The colourless solid which separated (3.4 g) was recrystallised from a mixture of ether and petroleum (b.p. 40°-60°). The product was identified as the required carboxylic acid, with a melting point of 156°-157°.

(d) Preparation of compound 49.

The acid from (c) (1.15 g) was converted to the acid chloride and reacted with methanesulphonamide in butyl acetate in the presence of caesium fluoride as described for compound 39 in paragraph (c) of Example 14. The product was recrystallised from isopropanol and had a melting point of 232°-233°.

EXAMPLE 19

This Example illustrates the preparation of N-methane-sulphonyl-5-(2-chloro-6-cyano-4-trifluoromethylphenoxy)-2-nitrobenzamide (compound 52 of Table I).

(a) Preparation of 3-carboxy-4-chloro-5-nitrobenzotrifluoride.

Concentrated nitric acid (15.5 ml) was added cautiously in portions to 4-chloro-3-cyanobenzotrifluoride (50 g) in concentrated sulphuric acid (150 ml). The solution was warmed to 75° C. when the reaction became exothermic; the solution was then heated to 95° for 1.5 hours, cooled, and poured into ice. The solid was collected, dried and recrystallised from chloroform to give the carboxylic acid with a melting point of 175°-178°.

(b) Preparation of 3-carbamoyl-4-chloro-5-nitro-benzotrifluoride.

The product from (a) (60 g) was heated under reflux in excess of thionyl chloride for 2.5 hours. The excess of thionyl chloride was removed under reduced pressure and the remaining oil taken up in toluene (100 ml) and slowly added with stirring to a concentrated solution of ammonia (200 ml; d 0.88) with cooling to keep the temperature below 20°. The mixture was extracted with ethyl acetate and the extract washed with water, dried (MgSO$_4$) and evaporated to give a light yellow solid. This was triturated with petroleum (b.p. 30°-40°) and collected (31 g). A portion recrystallised from chloroform had a melting point of 142°-143°.

(c) Preparation of 4-chloro-3-cyano-5-nitro-benzotrifluoride

The amide prepared in (b) (30 g) was heated under reflux in phosphorus oxychloride (100 ml) for 3 hours and the solution then cooled and poured on to ice. The solid which separated was collected and identified as the required cyano compound.

(d) Preparation of 3-amino-4-chloro-5-cyano-benzotrifluoride.

The cyano compound prepared in (c) (4 g) was dissolved in isopropanol (30 ml), and water (15 ml) and concentrated hydrochloric acid (1 drop) added. The solution was stirred and heated to 65° with iron dust (0.96 g) for 2 hours. The mixture was cooled and filtered. The filtrate was evaporated to give a solid (2.87 g) with a melting point of 102°, identified as the required amino compound.

(e) Preparation of 3-cyano-4,5-dichlorobenzotrifluoride

The amino compound prepared in (d) (2.8 g) was dissolved in concentrated hydrochloric acid (15 ml) and cooled to 0°. A solution of sodium nitrite (0.87 g) in the minimum of water was added in portions, keeping the temperature below 4°. The solution was then stirred at 0° for 15 minutes. Cuprous chloride (3 g, finely powdered) was then added in portions and the solution warmed to 40° C. over a period of 1 hour. The mixture was then cooled diluted with water, and extracted with ether. The ether extract was washed twice with dilute hydrochloric acid, dried (MgSO$_4$), and evaporated to give a yellow oil. This was taken up in a mixture of ether (1 volume) and hexane (4 volumes) and the solution filtered through chromatography grade silica gel. The filtrate was evaporated to give an oil (2.9 g) identified as the required dichloro compound.

(f) Preparation of 5-(2-chloro-6-cyano-4-trifluoromethylphenoxy) benzoic acid.

The product from (e) (2.3 g) was heated with 3-hydroxybenzoic acid (1.32 g) and anhydrous potassium carbonate (6 g) in dimethyl sulphoxide to 150° for 5.5 hours. The mixture was poured into water and the solution extracted with ether. The aqueous layer was then acidified (HCl) and extracted with ether. This extract was dried (MgSO$_4$) and evaporated to give a buff solid (1.52 g) identified as the required substituted benzoic acid.

(g) Preparation of 5-(2-chloro-6-cyano-4-trifluoromethyl-phenoxy-2-nitrobenzoic acid.

The carboxylic acid prepared according to paragraph (f) (2.0 g) in 1,2-dichloroethane (20 ml) was slowly added with stirring to concentrated sulphuric acid (20 ml) at 0°. Potassium nitrate (0.62 g) was added in small portions over a period of 20 minutes with cooling. The mixture was then stirred for another 30 minutes at 10° C. and poured into ice. The mixture was extracted with chloroform, and the extract washed with water, dried (MgSO$_4$), and evaporated to give an oil. Trituration with a mixture of ether and hexane gave a solid. This was purified by precipitation from ether solution by addition of hexane, and identified as the required nitro acid.

(h) Preparation of compound 52

The acid prepared according to paragraph (g) ) (1.2 g) was converted to its acid chloride and reacted with methanesulphonamide in the presence of pyridine as described for compound 42 (see paragraph (d) of Example 15). The product (0.42 g) had a melting point of 204°-205°.

EXAMPLE 20

This Example illustrates the preparation of N-methanesulphonyl-5-(2-chloro-6-fluoro-4-trifluoromethylphenoxy)-2-chlorobenzamide (compound 54 of Table I).

2-Chloro-5-hydroxybenzoic acid (1.5 g), 3-chloro-4,5-difluorobenzotrifluoride (1.88 g) and potassium carbonate (5 g) were heated with stirring to 80° for 2.5 hours. The mixture was agitated with ethyl acetate and dilute hydrochloric acid. The ethyl acetate layer was separated, washed with water, dried (MgSO$_4$), and evaporated to give a clear oil. Trituration with petroleum (b.p. 60°-80°) gave a solid (2.57 g) having a melting point of 134° C., identified as 2-chloro-5-(2-chloro-6-fluoro-4-trifluoromethylphenoxy)benzoic acid.

The benzoic acid derivative so prepared (1.09 g) was heated under reflux in thionyl chloride (20 ml) for 2.5 hours and the excess of thionyl chloride removed under reduced pressure. The remaining oil was taken up in dry pyridine (2 ml), cooled to 0° C. and methane sulphonamide (0.5 g) added. The solution was allowed to warm to room temperature and was then stirred for another 2 hours. The mixture was agitated with ethyl acetate and dilute hydrochloric acid. The ethyl acetate layer was dried (MgSO$_4$) and evaporated to give an oil which solidified on trituration with petroleum with petroleum (b.p. 30°-40°) and ether. The solid was twice recrystallised from a mixture of ether and petroleum to give N-methanesulphonyl 2-chloro-5(2-chloro-6-fluoro-4-trifluoromethylphenoxy)benzamide (0.36 g) with a melting point of 172°-173° C. The 3-chloro-4,5-difluorobenzotrifluoride used in the above process was prepared as follows:

2,6-Dichloro-4-trifluoromethylaniline (3.3 kg, prepared as in Example 15) in concentrated hydrochloric acid (25 liters) was stirred for 1 hour and then cooled to −6° C. A solution of sodium nitrite (1.41 kg) in water (3 liters) was added over a period of 4 hours keeping the temperature between −5° and −12°. The mixture was then stirred between −5° and 0° until all solid had dissolved (3.5 hours). The mixture was then added in 2 liter portions over a period of 35 minutes to a solution of cuprous chloride (1.5 kg) in concentrated hydrochloric acid with stirring. The dark solution was left to stand for 30 minutes, filtered, and extracted with dichloromethane (1×15 liters, then 2×10 liters). The extracts were washed with water (2×25 liters) dried (MgSO$_4$) and evaporated under reduced pressure to give 3,4,5-trichlorobenzotrifluoride (2.2 kg) with a boiling range of 98°-100°/40 Torr.

This trichloro compound (750 g) was added to a solution of potassium fluoride (900 g) in sulpholane (3.75 liters) which had previously been heated until liquid was distilling from the mixture at a still-head temperature of 270°, so as to dry the reactants. The flask was then fitted with a Vigreaux column (24" long) (61 cm) and a reflux divider. The mixture was heated under reflux for 5 hours, and the reflux divider then adjusted to collect liquid boiling at 120° or less. Heating was continued for 25 hours and 530 grams of distillate was collected. This was combined with a further quantity (520 g) of liquid obtained from a similar preparation. A portion (745 g) was distilled at atmospheric pressure after washing with water and drying (MgSo$_4$). The first runnings of distillate (b.p. 98°-106°) were pure 3,4,5-trifluorobenzotrifluoride (15 g). The next fraction (b.p. 106°-130°) contained a mixture of the trifluoro compound with some 3-chloro-4,5-difluorobenzotrifluoride (55 g). Finally, essentially pure 3-chloro-4,5-difluorobenzotrifluoride (b.p. 130°-136°) was collected (580 g).

The 2-chloro-5-(2-chloro-6-fluoro-4-trifluoromethylphenoxy)benzoic acid used above in the preparation of compound 54 is itself a new compound and forms a further part of the invention, together with its salts and esters. The compound, and its salts and esters, have herbicidal properties, and may be useful, for example, in the selective control of weeds in cotton crops. Rates of application may vary but are usually within the range from 0.25 to 5.0 kilograms per hectare. Application may be made by the conventional methods used for herbicides. Salts may be prepared for example by adding an equimolar amount of a base (e.g. an alkali or an amine) to an aqueous solution or suspension of the acid. Examples of salts include sodium, potassium, magnesium, calcium, ammonium, methylammonium, ethylammonium, and propylammonium salts. Esters may be prepared from the acid by conventional methods, for example by converting the acid to the acid chloride by heating under reflux with excess of thionyl chloride, isolating the acid chloride, and reacting it with an alcohol (e.g. methanol or ethanol). Examples of esters include the methyl, ethyl, propyl, butyl, pentyl and hexyl esters.

EXAMPLE 21

This Example illustrates the preparation of N-methanesulphonyl-5-(2,6-dichloro-4-trifluoromethylphenoxy)-2-chloro-benzamide (compound 56 of Table I).

3,5-Dichloro-4-fluorobenzotrifluoride (2.0 g), potassium carbonate (6.0 g) and 2-chloro-5-hydroxybenzoic acid (1.5 g) were heated and stirred in dry dimethylsulphoxide (25 ml) at 80° C. for 2.5 hours. The mixture was cooled and agitated with ethyl acetate and dilute hydrochloric acid. The ethyl acetate layer was washed with water, dried (MgSO$_4$), and evaporated under reduced pressure. The brown oil which remained was triturated with petroleum (b.p. 60°-80°) to give a white solid (2.3 g) identified as 2-chloro-5-(2,6-dichloro-4-trifluoromethylphenoxy)benzoic acid, with a melting point of 158°-159° C.

The benzoic acid derivative so prepared (1.0 g) was heated under reflux in thionyl chloride (15 ml) for 3 hours and the excess of thionyl chloride then removed under reduced pressure. The remaining oil was taken up in dry pyridine, the solution cooled to 0° C. and methanesulphonamide (0.8 g) added. The mixture was stirred at 0° C. for 1 hour, allowed to warm to room temperature, and stirred for another 2 hours. The mixture was then agitated with ether and dilute hydrochloric acid. The ether layer was separated, dried (MgSO$_4$) and evaporated to give an oil. This was triturated with a mixture of hexane and ether to give a white solid. This was taken up in ether and the solution washed three times with water, dried (MgSO$_4$) and evaporated to give an oil. This was triturated with hexane to give a solid. The solid was recrystallised from ether/hexane to give a white solid with a melting point of 195°-196° C. (melts and re-solidifies at 162° C.) identified as compound 56.

EXAMPLE 22

This Example illustrates an aqueous solution according to the invention.

| | |
|---|---|
| Compound No 1, as sodium salt | 100 g |
| Bentazon, sodium salt | 100 g |
| Water | to 1 liter |

The other ingredients are dissolved in the water.

EXAMPLE 23

This Example illustrates a dispersible powder formulation according to the invention.

| | |
|---|---|
| Compound No 7 | 100 g |
| Fluometuron | 400 g |
| 'Vanisperse' CB (dispersant) | 50 g |
| 'Aerosol' OT-B (wetter) | 20 g |
| Spestone (filler) | to 1 kg |

The above ingredients are ground together to produce a powdered mixture.

EXAMPLE 24

This Example illustrates an aqueous solution according to the invention.

| | |
|---|---|
| Compound no 1, sodium salt | 100 g |
| Alloxydim-sodium | 150 g |
| Water | to 1 liter |

The other ingredients are dissolved in the water.

EXAMPLE 25

This Example illustrates an emulsifiable concentrate according to the invention.

| | |
|---|---|
| Compound no 1 | 50 g |
| Butyl ester of 2[4(5-trifluoromethyl-pyridyl-2-oxy)phenoxy] propionic acid | 100 g |
| 'Lubrol' N 13 (emulsifier) | 50 g |
| 'Arylan' CA | 50 g |
| Acetophenone | to 1 liter |

The above ingredients are blended in a mixer.

Below is given the constitution of the materials represented in the above Examples by Trade Marks.

'Lubrol' N 13—nonyl phenol condensed with ethylene oxide
'Arylan' CA—solution of calcium dodecyl benzene sulphonate in butanol
'Aromasol' H—aromatic hydrocarbon
'Synperonic' NPE 1800—nonyl phenol condensed with propylene oxide and ethylene oxide
'Vanisperse' CB—sodium lignosulphonate
'Aerosol' OT-B—sodium dioctylsulphosuccinate plus sodium benzoate
'Spestone'—china clay

EXAMPLE 26

This Example illustrates the herbicidal activity of mixtures according to the invention. Compound no 1 of Table I was mixed with various known herbicides and dispersed in water to provide spray compositions. These were then sprayed on to pot plants at the 2 to 5 leaf growth stage in the greenhouse. The rates were generally lower than those which would be applied in the field, since the young greenhouse plants are generally more tender and susceptible to herbicides than plants growing out of doors. The spary volume used was equivalent to 200 liters per hectare.

The known herbicides were used in the form of their commercially available formulations. A surface-active agent (Agral 90, comprising a solution of a condensation product of p-nonylphenol with from 7-8 molar proportions of ethylene oxide in alcohol) was added to the spray compositions so that they contained 0.1% of Agral 90 in the final spray volume.

The damage to the plants was assessed 18 to 21 days after treatment, on a scale of 0 to 9 where 0 is 0 to 10% damage and 9 is 90 to 100%.

The known herbicides were as follows:
(A) Alloxydim-sodium
(B) Dichlofop-methyl (methyl ester of 2[4(2,4-dichlorophenoxy)phenoxy]propionic acid
(C) Ethyl ester of 4-methyl-4-(4-trifluoromethylphenoxybut-2-enoic acid
(D) Methyl ester of [4(4trifluoromethylphenoxy)-phenoxy]propionic acid
(E) Bentazon The results of the tests are given in Table 3 below.

TABLE 3

| Known Herbicide | Rate of Application kg/ha | Test Plants and Amount of Compound 1 Applied | | | | | | | | | | | | | | |
|---|---|---|---|---|---|---|---|---|---|---|---|---|---|---|---|---|
| | | No Compound 1 | | | | | 0.2 kg Compound 1 | | | | | 0.4 kg Compound 1 | | | | |
| | | Sy | Ip | Eh | Ec | Dg | Sy | Ip | Eh | Ec | Dg | Sy | Ip | Eh | Ec | Dg |
| A | 0 | — | — | — | — | — | 1 | 5 | 8 | 0 | 2 | 1 | 7 | 8 | 1 | 4 |
| | 0.3 | 0 | 0 | 2 | 8 | 6 | 2 | 4 | 9 | 7 | 6 | 2 | 7 | 9 | 9 | 7 |
| | 0.6 | 0 | 1 | 1 | 8 | 8 | 2 | 5 | 9 | 9 | 8 | 2 | 8 | 9 | 9 | 9 |
| B | 0 | — | — | — | — | — | 1 | 5 | 5 | 0 | 2 | 1 | 4 | 5 | 0 | 6 |
| | 0.375 | 1 | 1 | 4 | 9 | 1 | 2 | 5 | 5 | 9 | 1 | 2 | 4 | 6 | 7 | 6 |
| | 0.75 | 1 | 1 | 4 | 9 | 2 | 2 | 5 | 5 | 9 | 3 | 3 | 6 | 8 | 9 | 7 |
| C | 0 | — | — | — | — | — | 1 | 5 | 5 | 1 | 4 | 2 | 7 | 4 | 3 | 7 |
| | 0.25 | 0 | 0 | 3 | 9 | 9 | 3 | 7 | 6 | 9 | 9 | 2 | 7 | 6 | 9 | 9 |
| | 0.5 | 0 | 1 | 3 | 9 | 9 | 2 | 6 | 5 | 9 | 9 | 3 | 8 | 6 | 9 | 9 |
| D | 0 | — | — | — | — | — | 1 | 5 | 3 | 1 | 4 | 1 | 7 | 5 | 3 | 6 |
| | 0.5 | 1 | 2 | 2 | 9 | 9 | 3 | 8 | 6 | 9 | 9 | 3 | 9 | 7 | 9 | 9 |
| | 1.0 | 2 | 2 | 2 | 9 | 9 | 3 | 7 | 7 | 9 | 9 | 3 | 8 | 8 | 9 | 9 |
| E | 0 | — | — | — | — | — | 1 | 7 | 6 | 1 | 1 | 1 | 8 | 7 | 6 | 6 |
| | 0.2 | 0 | 0 | 1 | 0 | 0 | 2 | 7 | 6 | 2 | 2 | 2 | 9 | 7 | 7 | 4 |
| | 0.4 | 0 | 0 | 0 | 0 | 0 | 2 | 8 | 6 | 3 | 2 | 2 | 8 | 7 | 7 | 6 |

The names of the test plants were as follows:
Sy Soyabean, variety Amsoy
Ip *Ipomoea purpurea*
Eh *Euphorbia heterophylla*
Ec *Echinochloa crus-galli*

Dg *Digitaria sanguinalis*

A further test was carried out with mixtures of compound no 1 with 2-(4-trifluoromethylphenoxy)phenoxypropionic acid (common name trifop-methyl) and with the butyl ester of 2[4(5-trifluoromethylpyridyl-2-oxy)-phenoxy]propionic acid.

These compounds are coded F and G respectively in Table 4 below. Compound G was formulated as an emulsifiable concentrate having the following composition:

| COMPONENT | AMOUNT (grams per liter) |
|---|---|
| Compound G | 250 |
| Arylan CA | 25 |
| Geopon SF 365 | 25 |
| Aromasol H | to 1 liter |

Arylan SA is a Trade Mark for a composition comprising calcium dodecylbenenesulphonate. Geopon SF 365 is a Trade Mark for a composition comprising a condensate of castor oil with 40 molar proportions of ethylene oxide. Aromasol H is a Trade Mark for a solvnt comprising a mixture of trimethylbenzenes. The Mark for a surface-active agent comprising a condensate of 20 molar proportions of ethylene oxide with sorbitan monolaurate. The mixture of the compound and the emulsion was then shaken with glass beads and diluted to 40 ml with water. The spray composition so prepared was sprayed on to young pot plants (post-emergence test) of the species named in the Table below, at a rate equivalent to 1000 liters per hectare. Damage to plants was assessed 14 days after spraying by comparison with untreated plants, on a scale of 0 to 5 where 0 is 0 to 20% damage and 5 is complete kill. In the table of results, a dash (—) means that no test was made.

A test was also carried out to detect pre-emergence herbicidal activity. Seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 5.

The results of the tests are given in the Table below.

| RATE OF APPLICATION kg/ha | PRO-OR POST-EMERGENCE APPLICATION | TEST PLANTS | | | | | | | | | | | | | | | | | | | | | |
|---|---|---|---|---|---|---|---|---|---|---|---|---|---|---|---|---|---|---|---|---|---|---|---|
| | | Sb | Rp | Ct | Sy | Mz | Ww | Rc | Sn | Ip | Am | Pi | Ca | Xs | Ab | Ga | Co | Ot/Av | Dg | St | Ec | Sh | Ag | Cn | Al |
| 0.2 | Pre | 4 | 5 | 1 | 3 | 0 | 2 | 1 | 5 | 3 | 5 | — | 4 | 1 | 3 | — | 1 | 1 | 4 | 4 | 0 | 0 | 0 | — | 3 |
| 0.2 | Post | 4 | 5 | 3 | 3 | 3 | 4 | 1 | 5 | 4 | 5 | — | — | 3 | 5 | 3 | 3 | 4 | 4 | 5 | 5 | 3 | 2 | — | 4 |
| 1.0 | Pre | 5 | 5 | 3 | 4 | 0 | 4 | 1 | 5 | 4 | 5 | — | 5 | 2 | 5 | — | 3 | 2 | 5 | 5 | 4 | 4 | 5 | — | 5 |
| 1.0 | Post | 4 | 5 | 4 | 4 | 5 | 5 | 2 | 5 | 5 | 5 | — | — | 5 | 5 | 5 | 5 | 5 | 5 | 5 | 5 | 5 | 4 | | 5 | test was carried out as described above, but with a slightly different range of test plants. The two additional species were *Abutilon theophrasti (Ab)* and *Eleusine indica* (Ei). The results are given in Table 4 each figure is the average for three replicates, except the figures for *Eleusine indica* which are for two replicates.

NAMES OF TEST PLANTS

Sb: Sugar beet
Rp: Rape
Ct: Cotton
Sy: Soya Bean
Mz: Maize

TABLE 4

| Known Herbicide | Rate of Application kg/ha | Test Plants and Amount of Compound 1 Applied | | | | | | | | | | | | | | | |
|---|---|---|---|---|---|---|---|---|---|---|---|---|---|---|---|---|---|
| | | No Compound 1 | | | | | | 0.25 kg Compound 1 | | | | | | 0.5 kg Compound 1 | | | |
| | | Sy | Ip | Ab | Ec | Dg | Ei | Sy | Ip | Ab | Ec | Dg | Ei | Sy | Ip | Ab | Ec | Dg | Ei |
| F | 0 | — | — | — | — | — | — | 0.7 | 5.0 | 3.7 | 3.3 | 1.0 | 3.7 | 1.0 | 7.0 | 6.3 | 4.7 | 3.0 | 6.0 |
| | 0.5 | 1.0 | 1.7 | 0 | 2.3 | 9 | 9 | 2.7 | 7.7 | 5.3 | 5.7 | 9 | 9 | 3.3 | 8.7 | 9 | 6.7 | 9 | 9 |
| | 1.0 | 2.0 | 2.0 | 0 | 2.0 | 9 | 9 | 3.3 | 7.0 | 4.3 | 6.7 | 9 | 9 | 3.3 | 8.0 | 8.0 | 7.7 | 9 | 9 |
| | 2.0 | 2.0 | 2.0 | 1.3 | 3.0 | 9 | 9 | 3.0 | 8.7 | 7.7 | 7.0 | 9 | 9 | 3.7 | 8.7 | 9 | 7.0 | 9 | 9 |
| G | 0 | — | — | — | — | — | — | 1.7 | 6.7 | 6.3 | 4.0 | 8.0 | 6.0 | 1.3 | 8.3 | 8.3 | 8.7 | 8.7 | 7.0 |
| | 0.5 | 0 | 0.3 | 0.3 | 9 | 9 | 9 | 2.3 | 5.0 | 7.0 | 9 | 9 | 9 | 2.3 | 7.7 | 9 | 9 | 9 | 9 |
| | 1.0 | 0.7 | 1.3 | 1.0 | 9 | 9 | 9 | 2.3 | 8.0 | 8.3 | 9 | 9 | 9 | 3.3 | 8.0 | 9 | 9 | 9 | 9 |

EXAMPLE 27

This Example illustrates the herbicidal properties of 2-chloro-5-(2-chloro-6-fluoro-4-trifluoromethylphenoxy)benzoic acid. The compound was submitted to herbicide tests as described below.

The compound was formulated for test by mixing an appropriate amount of it with 5 ml of an emulsion prepared by diluting 160 ml of a solution containing 21.8 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Ww: Winter wheat
Rc: Rice
Sn: *Senecio vulgaris*
Ip: *Ipomoea purpurea*
Am: *Amaranthus retroflexus*
Pi: *Polygonum aviculare*
Ca: *Chenopodium album*
Xs: *Xanthium spinosum*
Ab: *Abutilon theophrasti*
Ga: *Galium aparine*
Co: *Cassia obtusifolia*

Ot/Av: Oats (cultivated in pre-emergence test and *Avena fatua* (wild oats) in post-emergence test).
Dg: *Digitaria sanguinalis*
St: *Setaria viridis*
Ec: *Echinochloa crus-galli*
Sh: *Sorghum halepense*
Ag: *Agropyron repens*
Cn: *Cyperus rotundus*
Al: *Alopecurus myosuroides*

What we claim is:

1. Diphenyl ether compounds of the formula:

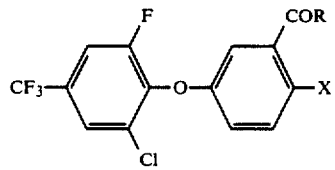

wherein X is a nitro group or a chlorine atom and R is:
(a) A group X'R$^3$ wherein X' is oxygen or sulphur, and R$^3$ is an aliphatic or alicyclic radical of up to 6 carbon atoms bearing one or more of the following substituents: halogen; nitro; hydroxy; CF$_3$; alkoxy; alkylthio, alkylsulphinyl, or alkylsulphonyl each having from 1 to 4 carbon atoms; phenyl; heterocyclyl containing 5 or 6 ring atoms; a group —NR$^1$R$^2$ as defined below; cyano; carboxy or a salt thereof; alkoxycarbonyl; a group —CONR$^1$R$^2$ wherein —NR$^1$R$^2$ is as defined below; formyl; alkanoyl having 2 to 5 carbon atoms; or a 1-pyrazolyl, 1-imidazolyl, 1-(1,2,4-triazolyl) or 2-(1,2,3-triazolyl) group optionally bearing one or more halogen, methyl, methoxy, or methylthio substituents;
(b) A group —NR$^1$R$^2$ wherein R$^1$ is hydrogen, an optionally substituted aliphatic radical of 1 to 6 carbon atoms or an optionally substituted alicyclic radical of 3 to 6 carbon atoms or an optionally substituted phenyl radical, and R$^2$ is defined as for R$^1$ but may additionally represent hydroxy; alkoxy of 1 to 4 carbon atoms; alkoxy of 1 to 4 carbon atoms substituted by phenyl or by carboxy or a salt, ester, or amide thereof, or alkoxy of 1 to 4 carbon atoms substituted by amino or mono- or di-dialkylamino wherein the alkyl groups have from 1 to 4 carbon atoms; or wherein the group —NR$^1$R$^2$ is constituted by an optionally methyl-substituted pyrrolidine, piperidine, or morpholine ring, or by a succinimido, or phthalimido radical or by a group of the formula:

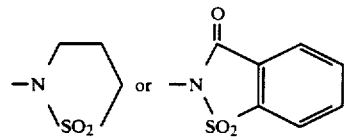

or
(c) a phenoxy, phenylthio, 2-nitrophenoxy, or 2-sulpholanoxy group, or a group —ON=C(CH$_3$)$_2$.

2. A compound as claimed in claim 1 wherein R is a group X'R$^3$ which comprises an alkoxy radical of 1 to 6 carbon atoms substituted by a halogen atom; a nitro group; a carboxyl group or a salt or C$_{1-6}$ alkyl ester thereof; or an optionally chloro, methyl, or methoxy susbstituted 1-imidazolyl, 1-(1,2,4-triazolyl), or 1-pyrazolyl group.

3. A compound as claimed in claim 1 wherein R is a group X'R$^3$ which comprises a phenoxy or phenylthio group optionally substituted by nitro.

4. A compound as claimed in claim 1 wherein R is a group NR$^1$R$^2$ wherein R$^1$ is hydrogen or alkyl of 1 to 6 carbon atoms and R$^2$ is hydrogen, alkoxy of 1 to 6 carbon atoms, or alkoxy of 1 to 6 carbon atoms substituted by carboxy or a salt or C$_{1-6}$ alkyl ester thereof, or wherein the group —NR$^1$R$^2$ is constituted by an optionally methyl-substituted pyrrolidine, piperidine or morpholine ring, or by a succinimido or phthalimido radical, or by a group of the formula:

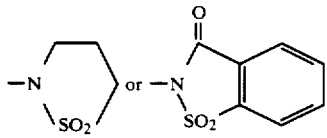

* * * * *